US012128094B2

(12) United States Patent
Contorni et al.

(10) Patent No.: US 12,128,094 B2
(45) Date of Patent: Oct. 29, 2024

(54) IMMUNOGENIC COMPOSITIONS COMPRISING OMVS, AN ACELLULAR PERTUSSIS ANTIGEN, A TETANUS TOXOID AND A DIPHTHERIA TOXOID

(71) Applicant: GLAXOSMITHKLINE BIOLOGICALS SA, Rixensart (BE)

(72) Inventors: Mario Contorni, Siena (IT); Mariagrazia Pizza, Siena (IT); Anja Seubert, Siena (IT)

(73) Assignee: GlaxoSmithKline Biologicals SA, Rixensart (BE)

( * ) Notice: Subject to any disclaimer, the term of this patent is extended or adjusted under 35 U.S.C. 154(b) by 681 days.

(21) Appl. No.: 17/287,268

(22) PCT Filed: Nov. 4, 2019

(86) PCT No.: PCT/EP2019/080120
§ 371 (c)(1),
(2) Date: Apr. 21, 2021

(87) PCT Pub. No.: WO2020/094580
PCT Pub. Date: May 14, 2020

(65) Prior Publication Data
US 2023/0201325 A1 Jun. 29, 2023

(30) Foreign Application Priority Data
Nov. 6, 2018 (EP) .................................... 18204691

(51) Int. Cl.
*A61P 31/04* (2006.01)
*A61K 39/00* (2006.01)

(52) U.S. Cl.
CPC .......... *A61K 39/0018* (2013.01); *A61P 31/04* (2018.01); *A61K 2039/55505* (2013.01)

(58) Field of Classification Search
None
See application file for complete search history.

(56) References Cited

U.S. PATENT DOCUMENTS

| | | | | |
|---|---|---|---|---|
| 2014/0302558 A1* | 10/2014 | Boonchird ............. | A61K 38/00 435/69.3 |
| 2015/0224185 A1* | 8/2015 | Contorni .............. | A61K 39/092 424/197.11 |
| 2016/0193322 A1* | 7/2016 | Steff .................... | A61K 39/385 424/186.1 |

FOREIGN PATENT DOCUMENTS

| | | | |
|---|---|---|---|
| EP | 2 258 387 A2 | 12/2010 |
| JP | 2016-510056 A | 4/2016 |
| JP | 2016-527294 A | 9/2016 |
| WO | WO 2014/135651 A1 | 9/2014 |
| WO | WO 2014/155294 A1 | 10/2014 |
| WO | WO 2015/018806 A1 | 2/2015 |
| WO | WO 2018/167061 A1 | 9/2018 |

OTHER PUBLICATIONS

Marr et al. Infect. Immun. May 2010; 78(5):2060-2069.*
"Instructions for use of the drug INFANRIX® HEXA (Vaccine for the prevention of diphtheria, tetanus, pertussis (cell-free), polio (inactivated), hepatitis B combined and adsorbed, completed with a vaccine for the prevention of infection caused by Haemophilus influenzae type b conjugated and adsorbed)," found from the Internet, <URL: https://grls.rosminzdrav.ru/Grls_View_v2.aspx?routingGuid=bbc7c2e1-1e34-4b4f-b11a-e185066cd41a>, Jan. 26, 2023, 18 pages total.
Eurasian Office Action for Eurasian Application No. 202190914, dated Jan. 27, 2023, with an English translation.
Gasperini, ""Approaches to new generation vaccines against pertussis and identification of new virulence factors"", Dottorato Di Ricerca in Biologia Cellulare E Molecolare Ciclo XXIX, Dec. 1, 2017, XP055650997, Retrieved from the Internet: URL:http://amsdottorato unibo it/8029/1/Gasperini%20 %20PhD%20thesis pdf [retrieved on Dec. 9, 2019], pp. 1-84.
Guiso, "Bordetella Adenylate Cyclase-Hemolysin Toxins", Toxins, vol. 9, No. 9, Sep. 11, 2017, pp. 277-291 (Total p. 13).
International Search Report issued in PCT/EP2019/080120 (PCT/ISA/210), dated Jan. 2, 2020.
Raeven et al., "Immunoproteomic Profiling of Bordetella pertussis Outer Membrane Vesicle Vaccine Reveals Broad and Balanced Humoral Immunogenicity", Journal of Proteome Research, vol. 14, No. 7, Jun. 2, 2015, pp. 2929-2942.
Seubert et al., "Genetically detoxified pertussis toxin (PT-9K/129G): implications for immunization and vaccines", Expert Review of Vaccines, vol. 13, No. 10, Oct. 4, 2014, pp. 1191-1204.
Written Opinion of the International Searching Authority issued in PCT/EP2019/080120 (PCT/ISA/237), dated Jan. 2, 2020.
English translation of "Instructions on the use of a medicinal product for medical use of INFANRIX® HEXA (vaccine for the prevention of diphtheria, tetanus, whooping cough (acellular), polio (inactivated), hepatitis B, combined, adsorbed in combination with a vaccine for the prevention of infection caused by Haemophilus influenzae type b conjugated, adsorbed)," retrieved from the Internet https://grls.rosminzdrav.ru/Grls_View_v2.aspx?routingGuid=bbc7c2e1-1e34-4b4f-b11ae185066cd41a. , dated Jan. 26, 2023, 11 pages total.

(Continued)

*Primary Examiner* — Oluwatosin A Ogunbiyi

(57) ABSTRACT

The invention provides an immunogenic composition comprising OMVs and (a) acellular pertussis antigen, (b) a tetanus toxoid and (c) a diphtheria toxoid, wherein the OMVs are derived from *Bordetella pertussis*. The invention also provides compositions for use in a method for raising an immune response in a patient, comprising the step of administering to the patient a composition of the invention.

19 Claims, 19 Drawing Sheets

Specification includes a Sequence Listing.

(56) References Cited

OTHER PUBLICATIONS

Eurasian Office Action for Eurasian Application No. 202190914, dated Jan. 27, 2023, with English translation.
Rolin et al., "Enzymatic Modification of Lipid A by ArnT Protects Bordetella bronchiseptica against Cationic Peptides and Is Required for Transmission," Infection and Immunity, vol. 82, No. 2, Feb. 2014, pp. 491-499.

* cited by examiner (a) HEK293-hTLR4 cells (b) human PBMCs (IL-6)

Area under the curve:

| PBS | wP | OMV 0.4 | OMV 2 | OMV 10 |
|---|---|---|---|---|
| 75.25 | 11.94 | 48.93 | 35.89 | 29.77 |

Area under the curve:

| PBS | wP | aP | aP+OMV | OMV |
|---|---|---|---|---|
| 73.73 | 8.479 | 37.72 | 15.17 | 31.83 |

SEQUENCE LISTING

```
<160> NUMBER OF SEQ ID NOS: 4

<210> SEQ ID NO 1
<211> LENGTH: 29
<212> TYPE: DNA
<213> ORGANISM: Artificial Sequence
<220> FEATURE:
<223> OTHER INFORMATION: Synthetic primer

<400> SEQUENCE: 1

atagaattca cgcggtgcgg cgccagcgc                                        29
```

-continued

```
<210> SEQ ID NO 2
<211> LENGTH: 28
<212> TYPE: DNA
<213> ORGANISM: Artificial Sequence
<220> FEATURE:
<223> OTHER INFORMATION: Synthetic primer

<400> SEQUENCE: 2

ataggatccg ccaggacctg gcctggcc                                      28


<210> SEQ ID NO 3
<211> LENGTH: 29
<212> TYPE: DNA
<213> ORGANISM: Artificial Sequence
<220> FEATURE:
<223> OTHER INFORMATION: Synthetic primer

<400> SEQUENCE: 3

ataggatccg gacgaagcct tcaaggggc                                     29


<210> SEQ ID NO 4
<211> LENGTH: 28
<212> TYPE: DNA
<213> ORGANISM: Artificial Sequence
<220> FEATURE:
<223> OTHER INFORMATION: Synthetic primer

<400> SEQUENCE: 4

ataaagcttc gtccaggcgc gccagcgc                                      28
```

IMMUNOGENIC COMPOSITIONS COMPRISING OMVS, AN ACELLULAR PERTUSSIS ANTIGEN, A TETANUS TOXOID AND A DIPHTHERIA TOXOID

REFERENCE TO SEQUENCE LISTING SUBMITTED VIA EFS-WEB

This application includes an electronically submitted sequence listing in .txt format. The .txt file contains a sequence listing entitled "2021-10-23_2801-0360PUS1_ST25.txt" created on Oct. 23, 2021 and is 1,065 bytes in size. The sequence listing contained in this .txt file is part of the specification and is hereby incorporated by reference herein in its entirety.

TECHNICAL FIELD

This invention is in the field of combination vaccines, that is vaccines containing a mixture of immunogens from more than one pathogen, such that administration of the vaccine can simultaneously immunize a subject against more than one pathogen. More particularly, the invention relates to booster vaccines for diphtheria, tetanus and pertussis.

BACKGROUND OF THE INVENTION

Vaccines containing antigens from more than one pathogenic organism within a single dose are known as "multivalent" or "combination" vaccines. Combination vaccines offer patients the advantage of receiving a reduced number of injections, which can lead to a clinical advantage of increased compliance (e.g. see chapter 29 of reference 1). Various combination vaccines have been approved for human use in the EU and the USA, including trivalent vaccines for protecting against diphtheria, tetanus and pertussis. Such vaccines may be referred to as DTaP and Tdap. Whilst DTaP and TdaP are both combined vaccines against diphtheria, tetanus, and pertussis, DTaP vaccines are used for primary immunisation whilst TdaP vaccines are used for subsequent, booster vaccinations. The difference between the primary and booster vaccine compositions is in the dosage. More particularly, with regard to booster vaccines, generally these vaccines comprise lower doses of some antigen components, for example, the diphtheria toxoid content of BOOSTRIX is 10-fold lower than than that of INFANRIX. This is indicated by use of the lower case letter 'd' referring to a lower amount of diphtheria toxoid.

The ratio of antigenic components may also be altered. For example, the ratio of diphtheria and tetanus toxoids is 2.5:1 in INFANRIX but is 1:2 in BOOSTRIX. Thus these booster vaccines show a large reduction in the dose of diphtheria toxoid, both in absolute amounts and also relative to the tetanus toxoid content.

However, in recent years, resurgence in disease caused by *Bordetella pertussis* has been observed even in countries with high vaccine coverage. Whilst the precise reasons for this recurrence are not clear, potential causes include waning immunity and epidemiological changes in the circulating strains.

Therefore, it is an object of the invention to provide further and improved combination vaccines for protecting against *Corynebacterium diphtheriae, Clostridium tetani* and *Bordetella pertussis*. It is also an object of the invention to provide further and improved TdaP vaccines suitable for human use as a booster in adults, adolescents and children aged four years and older who have previously received childhood immunisation.

SUMMARY OF THE INVENTION

The invention is based on studies of combination vaccines that comprise outer membrane vesicles (OMVs) from *Bordetella pertussis*. The inventors have found that these combination vaccines elicit specific antibody titers to the corresponding antigens with little or no immunological interference between the various antigens. The presence of OMVs from *Bordetella pertussis* provides an improved antibody response against *Bordetella* and surprisingly also improves the antibody response against other antigens in the composition.

Thus, in a first aspect there is provided an immunogenic composition comprising (a) an Outer Membrane Vesicle (OMV), (b) an acellular pertussis antigen, (c) a tetanus toxoid and (d) a diphtheria toxoid, wherein the OMV is derived from *Bordetella pertussis*. Particularly the OMV is derived from a *Bordetella pertussis* strain expressing a genetically detoxified pertussis toxoid. More particularly the OMV is derived from a *Bordetella pertussis* strain expressing the genetically detoxified pertussis toxoid PT 9K/129G.

Thus, the invention provides an immunogenic composition comprising (a) *Bordetella pertussis* Outer Membrane Vesicles (OMVs), (b) an acellular pertussis antigen, (c) a tetanus toxoid and (d) a diphtheria toxoid, wherein the OMVs are derived from a *Bordetella pertussis* strain expressing a genetically detoxified pertussis toxoid, particularly the genetically detoxified pertussis toxoid PT 9K/129G.

The invention further provides an immunogenic composition comprising (a)*Bordetella pertussis* Outer Membrane Vesicles (OMVs) comprising genetically detoxified pertussis toxoid, particularly PT 9K/129G, (b) an acellular pertussis antigen, (c) a tetanus toxoid and (d) a diphtheria toxoid.

The invention yet further provides an immunogenic composition comprising (a) *Bordetella pertussis* Outer Membrane Vesicles (OMVs) comprising genetically detoxified pertussis toxoid, particularly PT 9K/129G, wherein Lipid A in the OMVs has a modified structure lacking glucosamine (GlcN) substitutions on the distal phosphate groups of the core structure, (b) an acellular pertussis antigen, (c) a tetanus toxoid and (d) a diphtheria toxoid.

The PT-9K/129G genetically detoxified pertussis toxoid comprises two amino acid substitutions within the S1 subunit, specifically R9K and E129G (see for example EP0396964). Thus, still yet more particularly, the OMVs are derived from a *Bordetella pertussis* strain that comprises an S1 gene which has been modified to include the mutations R9K and E129G and expresses the genetically detoxified pertussis toxoid PT-9K/129G. Yet more particularly, 100% of the pertussis toxoid in the Outer Membrane Vesicles is genetically detoxified PT, particularly PT 9K/129G.

In some embodiments, *Bordetella pertussis* OMVs used with the invention have a modified lipidA structure lacking glucosamine (GlcN) substitutions on the distal phosphate groups of the core structure. In some embodiments, the *Bordetella pertussis* strain from which OMVs are obtained comprises a knock-out of ArnT, particularly deletion of the ArnT encoding gene (ΔArnT). Thus, OMVs used with the invention and derived from such strains may have a modified lipidA structure lacking glucosamine (GlcN) substitutions on the distal phosphate groups of the core structure.

Particularly, the OMVs used with the invention are not treated with formaldehyde, formalin, glutaraldehyde, hydrogen peroxide or a combination thereof. More particularly, OMVs used with the invention are not chemically detoxified by treatment with formaldehyde, formalin, glutaraldehyde, hydrogen peroxide or a combination thereof.

Suitable acellular pertussis antigens include detoxified pertussis toxin (PT), filamentous hemagglutinin (FHA), pertactin (PRN), fimbrial protein 2 (FIM2), fimbrial protein 3 (FIM3) and combinations thereof. In certain embodiments the acellular pertussis antigen comprises at least two, for example, at least three antigens selected from the group consisting of detoxified pertussis toxin (PT), filamentous hemagglutinin (FHA), pertactin (PRN), fimbrial protein 2 (FIM2), fimbrial protein 3 (FIM3) Particular combinations of acellular pertussis antigens for use in the invention include: (1) PT, FHA and PRN; (2) PT, FHA, PRN, FIM2 and FIM3; (3) PT and FHA and (4) PT, FHA, FIM2 and FIM3.

Particularly, the immunogenic composition is a vaccine. More particularly, the vaccine is for administration to a human. The vaccine may be for primary immunisation. Yet more particularly the vaccine is for use as a booster, for example, in secondary immunisation. Still yet more particularly the diphtheria toxoid is present at a concentration of from about 4 Lf/ml to about 8 Lf/ml. More particularly, the diphtheria toxoid is present at a concentration of about 2 Lf per 0.5 ml dose, about 2.5 Lf per 0.5 ml dose, about 3 Lf per 0.5 ml dose, about 3.5 Lf per 0.5 ml dose or about 4 Lf per 0.5 ml dose. The tetanus toxoid may be present at a concentration of about 5 Lf per 0.5 ml dose.

Particularly the tetanus toxoid and diphtheria toxoid are present at a tetanus toxoid:diphtheria toxoid ratio of from 1.5:1 to 2.5:1 (measured in Lf units), for example about 2:1 (measured in Lf units).

The immunogenic composition may comprise an adjuvant, particularly an aluminium salt adjuvant.

In a second aspect of the invention, there is provided an immunogenic composition for use in a method of raising an immune response in a patient, comprising the step of administering to the patient an immunogenic composition according to the present invention.

In a third aspect of the invention, there is provided a process for preparing an immunogenic composition according to the present invention, comprising mixing a first component comprising the Outer Membrane Vesicle (OMV) and a second component comprising the acellular pertussis antigen, the tetanus toxoid and the diphtheria toxoid. In certain embodiments of the third aspect of the invention, the OMV in the first component is lyophilised and the second component comprises antigens in aqueous form. Thus, the process may further comprise the step of reconstituting the lyophilised OMV in the first component with the aqueous antigens of the second component.

In a fourth aspect of the invention, there is provided a kit for preparing the immunogenic composition according to the present invention, comprising a first component comprising the OMV and a second component comprising the acellular pertussis antigen, the tetanus toxoid and the diphtheria toxoid, wherein the two components are in separate containers. In certain embodiments of the fourth aspect of the invention, the OMV in the first component is lyophilised and the second component comprises antigens in aqueous form.

BRIEF DESCRIPTION OF FIGURES

FIG. 1(*a*) results from the Luciferase reporter gene assay for hTLR4 activation with W28 9K/129G (Bp WT) and the W28 9K/129G arntKO (Bp ΔarnT). Different concentrations of bacteria were used to stimulate HEK293 cells, fold induction compared to PBS is reported. FIG. 1(*b*): ELISA for IL-6 detection in human PBMCs supernatants following stimulation with different concentrations of bacteria.

FIG. 3(*a*): Anti-FHA IgG titres; FIG. 3(*b*): Anti-69K IgG titres; FIG. 3(*c*): Anti-PT IgG titres.

FIG. 7(*c*) Single immunisation with OMV promotes A pertussis-specific Th1/Th17 responses. Spleen cells ($2\times10^6$/mL) from vaccinated C57BL6 mice were cultured in the presence of sonicated *B. pertussis* (SBP, 5 μg/mL). After 72 hours the concentration of IFNγ (TH1-indicator), IL-13 (TH2-indicator), and IL-17 (TH17 indicator) in the supernatants was analysed by ELISA.***$p<0.001$.

DETAILED DESCRIPTION OF THE INVENTION

Figure 1:
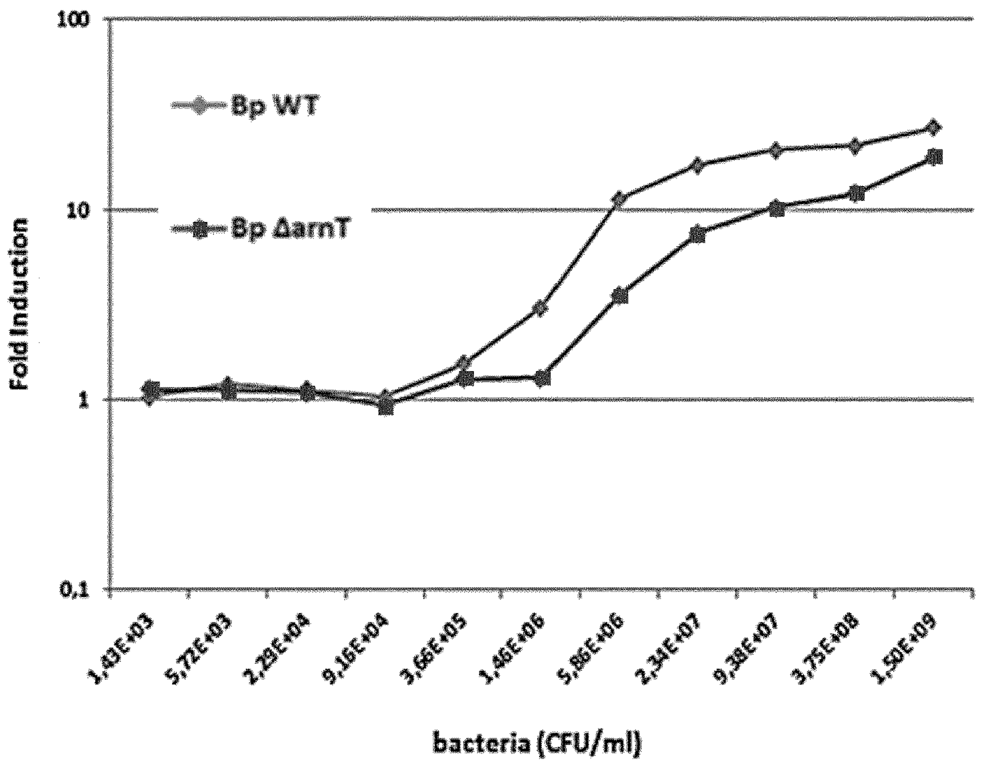
FIG. 1: In vitro reactogenicity of W28 9K/129G ΔarnT compared to W28 9K/129G vaccine strains.
Figure 1:
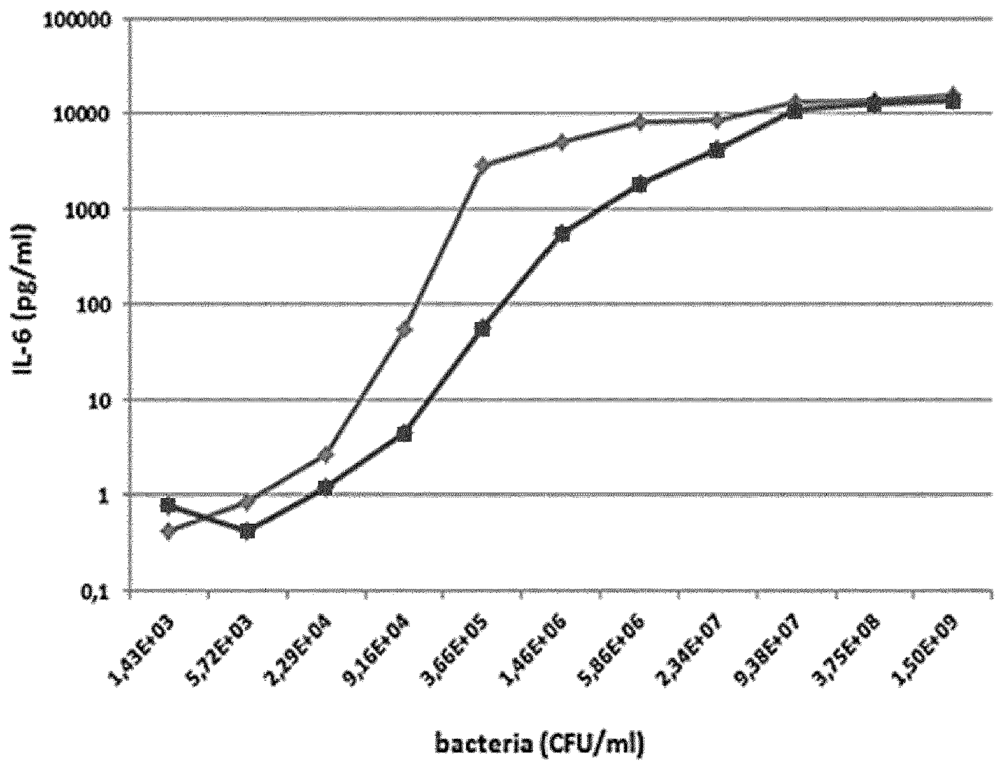

The invention is based on studies of compositions that comprise outer membrane vesicles (OMVs) derived from *Bordetella pertussis*. The inventors have found that immunogenic compositions comprising both OMVs and antigens such as acellular pertussis antigens are capable of inducing an immune response greater than that seen following immunisation with either OMVs alone or acellular pertussis antigens alone. In addition, OMVs also improve the immune response to other non-*Bordetella* antigens, such as tetanus toxoid and diphtheria toxoid. Use of the term "derived from" refers to the source of the OMV as originating from *Bordetella pertussis*, i.e. the bacterial strain from which the OMVs are produced or originated. As such, the present invention provides an immunogenic composition comprising (a) a *Bordetella pertussis* OMV, (b) an acellular pertussis antigen, (c) a tetanus toxoid and (d) a diphtheria toxoid.

The term "immunogenic composition" broadly refers to any composition that may be administered to elicit an immune response, such as an antibody or cellular immune response, against an antigen present in the composition. Thus compositions of the invention are immunogenic. When the immunogenic compositions prevent, ameliorate, palliate or eliminate disease from the subject, then such compositions may be referred to as a vaccine. Vaccines according to the invention are preferably prophylactic (i.e. to prevent infection). Prophylactic vaccines do not guarantee complete protection from disease because even if the patient develops antibodies, there may be a lag or delay before the immune system is able to fight off the infection. Therefore, and for the avoidance of doubt, the term prophylactic vaccine may also refer to vaccines that ameliorate the effects of a future infection, for example by reducing the severity or duration of such an infection. The terms "protection against infection" and/or "provide protective immunity" means that the immune system of a subject has been primed (e.g by vaccination) to trigger an immune response and repel infection. Particularly, the immune response triggered is capable of repelling infection against a number of pathogens, such as different strains of bacteria. A vaccinated subject may thus get infected, but is better able to repel the infection than a control subject.

OMVs

OMVs are well known in the art and are spontaneously released into culture medium by bacteria. OMVs contain components, such as protein and lipid components, of the bacterial outer membrane of the cultured bacteria. 'Native OMVs' ('nOMVs' [2]), and detergent-extracted OMVs (dOMVs), all form part of the invention and are collectively referred to as OMVs herein. The term "generalized module for membrane antigens" may also be used to refer to OMVs obtained from mutant bacteria. In some embodiments of the invention, the OMVs are native OMVs.

OMVs may be obtained from a culture of *Bordetella pertussis*. OMVs are prepared from the outer membrane of cultured bacteria. The vesicles can be obtained by disruption of or natural 'blebbing' from the outer membrane of the bacterium to form vesicles therefrom.

They may be obtained from bacteria grown in broth or in solid medium culture, for example by separating the bacterial cells from the culture medium (e.g. by filtration or by a low-speed centrifugation to pellet the cells), lysing the cells (without detergent), and separating an outer membrane fraction from cytoplasmic molecules (e.g. by filtration, by differential precipitation or aggregation of outer membranes and/or OMVs, by affinity separation methods using ligands that specifically recognize outer membrane molecules, or by a high-speed centrifugation that pellets outer membranes and/or OMVs).

OMVs may also be prepared artificially from *Bordetella pertussis*, for example using detergent treatment (e.g. with deoxycholate or sarkosyl) or by non-detergent means (e.g. see reference 3). Techniques for artificially forming OMVs include treating bacteria with a bile acid salt detergent (e.g. salts of lithocholic acid, chenodeoxycholic acid, ursodeoxycholic acid, deoxycholic acid, cholic acid, ursocholic acid, etc., with sodium deoxycholate [4 & 5]) at a pH sufficiently high not to precipitate the detergent [6]. Other techniques may be performed substantially in the absence of detergent [3] using techniques such as sonication, homogenisation, microfluidisation, cavitation, osmotic shock, grinding, French press, blending, etc.

A useful process for OMV preparation is described in reference 7 and involves ultrafiltration of crude OMVs, rather than instead of high speed centrifugation. The process may involve a step of ultracentrifugation after the ultrafiltration takes place.

Preparations of OMVs used in the present invention will generally be substantially free from whole bacteria, whether living or dead. The size of the vesicles means that they can readily be separated from whole bacteria by filtration e.g. as typically used for filter sterilisation.

The OMV is capable of eliciting an immune response to *Bordetella pertussis* when administered to a mammal. The immune response may be a cellular or a humoral immune response. Particularly, the immune response is an antibody response. Yet more particularly the immune response is a T-cell immune response that can neutralise the infection and/or virulence of *Bordetella pertussis*. The immune response elicited by the OMV may be directed toward or against one or more *B. pertussis* protein antigens present in the OMV.

Despite being a secreted toxin, pertussis toxin is present in OMVs, for example, derived from the periplasmic space. As a result, OMVs used in the art have been treated with chemical agents such as formalin to chemically detoxify any PT. In addition to issues with removing residual formalin, chemical treatment may negatively impact immunogenicity of OMVs, for example by protein cross-linking.

The use of OMVs derived from a *Bordetella pertussis* strain expressing a genetically detoxified pertussis toxoid is therefore advantageous and has not been suggested in the art. Particularly advantageous are OMVs derived from a *Bordetella pertussis* strain expressing the genetically detoxified pertussis toxoid PT 9K/129G. In particular, for use in the present invention, the Inventors have isolated OMVs from a *Bordetella pertussis* strain that comprises an S1 gene which has been modified to include the mutations R9K and E129G and that expresses the genetically detoxified pertussis toxoid PT-9K/129G. Thus, chemical detoxification of OMVs by treatment with chemicals such as formaldehyde, formalin, glutaraldehyde, hydrogen peroxide and combinations thereof is not necessary. Particularly, OMVs of the invention are not chemically detoxified, more particularly OMVs of the invention are not chemically detoxified and/or treated with formaldehyde, formalin, glutaraldehyde, hydrogen peroxide and combinations thereof.

The use of *Bordetella pertussis* strains in which the ArnT gene has been knocked-out or deleted is also advantageous. OMVs derived from such strains comprise Lipid A that has a modified structure without glucosamine (GlcN) substitutions on the distal phosphate groups of the core structure. As a result, these OMVs exhibit a decreased level of TLR4 activation when compared to OMVs derived from strains with a functional ArnT gene.

Immunogenic compositions of the invention comprise both an OMV component (a) and an acellular pertussis antigen component (b). The outer membrane vesicle component (a) comprises many proteins, associated with the membrane or contained within the OMVs including, for example, small amounts of PT, FHA or pertactin. However, these OMV associated components should not be construed to be the acellular pertussis antigen component (b), described below, which generally will be provided separately from the OMVs in purified form, for example, as isolated recombinant protein antigen(s).

In some embodiments of the invention, compositions comprising OMVs derived from *Bordetella parapertussis* are excluded from the invention.

Diphtheria Toxoid

Diphtheria is caused by *Corynebacterium diphtheriae*, a Gram-positive non-sporing aerobic bacterium. This organism expresses a prophage-encoded ADP-ribosylating exotoxin ('diphtheria toxin'), which can be treated (e.g. using formaldehyde) to give a toxoid that is no longer toxic but that remains antigenic and is able to stimulate the production of specific anti-toxin antibodies after injection. Diphtheria toxoids are disclosed in more detail in chapter 13 of reference 8. Preferred diphtheria toxoids are those prepared by formaldehyde treatment. The diphtheria toxoid can be obtained by growing *C.diphtheriae* in growth medium (e.g. Fenton medium, or Linggoud & Fenton medium), which may be supplemented with bovine extract, followed by formaldehyde treatment, ultrafiltration and precipitation. The toxoided material may then be treated by a process comprising sterile filtration and/or dialysis.

Quantities of diphtheria toxoid can be expressed in international units (IU). For example, the NIBSC [9] supplies the 'Diphtheria Toxoid Adsorbed Third International Standard 1999' [10,11], which contains 160 IU per ampoule. As an alternative to the IU system, the 'Lf' unit ("flocculating units", the "limes flocculating dose", or the "limit of flocculation") is defined as the amount of toxoid which, when mixed with one International Unit of antitoxin, produces an optimally flocculating mixture [12]. For example, the NIBSC supplies 'Diphtheria Toxoid, Plain' [13], which contains 300 Lf per ampoule, 'The 1st International Reference Reagent For Diphtheria Toxoid For Flocculation Test' [14] which contains 900 Lf per ampoule. The conversion between IU and Lf systems depends on the particular toxoid preparation.

Where bovine materials are used in the culture of *C.diphtheriae*, they should be obtained from sources that are free from bovine spongiform encephalopathy (BSE) or from other transmissible spongiform encephalopathies (TSEs).

The diphtheria toxoid in the immunogenic compositions of the invention is typically present in an amount that is capable of eliciting an immune response when administered. Ideally, diphtheria toxoid can elicit a protective immune response. The amount of diphtheria toxoid in the immunogenic compositions of the invention is typically 1-50 Lf/dose. Booster vaccines for adolescents and adults typically contain between 4 Lf/ml and 8 Lf/ml of diphtheria toxoid, e.g. 2.5 Lf, preferably 4 Lf, per 0.5 ml dose. Paediatric vaccines typically contain between 20 and 50 Lf/ml of diphtheria toxoid, e.g. 10 Lf or 25 Lf per 0.5 ml dose.

For paediatric combination vaccines, the ratio of diphtheria toxoid to tetanus toxoid is typically greater than 1 (i.e. paediatric vaccines usually have an excess of diphtheria toxoid) and generally between 2:1 and 3:1 (measured in Lf units), e.g. 2.5:1. In contrast, for booster vaccine that are administered to adolescents or adults (who usually have received at least one paediatric combination vaccine comprising diphtheria toxoid and tetanus toxoid), the ratio of tetanus toxoid to diphtheria toxoid is typically greater than 1 (i.e. booster vaccines usually have an excess of tetanus toxoid) and generally between 1.5:1 and 2.5:1, e.g. 2:1. The diphtheria toxoid is typically unconjugated.

The total amount of diphtheria toxoid may be equivalent to 1-50 Lf/dose, for example, in Booster vaccines at a concentration of between 4 Lf/ml and 8 Lf/ml, for example 2.5 Lf per 0.5 ml dose or 4 Lf per 0.5 ml dose; in paediatric vaccines at a concentration of between 20 and 50 Lf/ml, for example 10 Lf per 0.5 ml dose or 25 Lf per 0.5 ml dose. In particular embodiments where chemically detoxified diphtheria toxoid is absent, the amount of genetically detoxified diphtheria toxoid, particularly CRM197, present may be equivalent to 1-50 Lf/dose, at a concentration, for example in booster vaccines, of between 4 Lf/ml and 8 Lf/ml, for example 2.5 Lf per 0.5 ml dose or 4 Lf per 0.5 ml dose, and in paediatric vaccines at a concentration of between 20 and 50 Lf/ml, for example 10 Lf per 0.5 ml dose or 25 Lf per 0.5 ml dose.

The diphtheria toxoid may be adsorbed onto an aluminium hydroxide adjuvant.

Typically, the immunogenic composition comprising diphtheria toxoid antigen is substantially free from any mercurial preservatives.

Tetanus Toxoid

Tetanus is caused by *Clostridium tetani*, a Gram-positive, spore-forming *bacillus*. This organism expresses an endopeptidase ('tetanus toxin'), which can be treated to give a toxoid that is no longer toxic but that remains antigenic and is able to stimulate the production of specific anti-toxin antibodies after injection. Tetanus toxoids are disclosed in more detail in chapter 27 of reference 1. Preferred tetanus toxoids are those prepared by formaldehyde treatment. The tetanus toxoid can be obtained by growing *C.tetani* in growth medium (e.g. a Latham medium derived from bovine casein), followed by formaldehyde treatment, ultrafiltration and precipitation. The material may then be treated by a process comprising sterile filtration and/or dialysis.

Quantities of tetanus toxoid can be expressed in international units (IU). For example, the NIBSC [15] supplies the 'Tetanus Toxoid Adsorbed Third International Standard 2000' [16,17], which contains 469 IU per ampoule. As an alternative to the IU system, the 'Lf' unit is defined as the amount of toxoid which, when mixed with one International Unit of antitoxin, produces an optimally flocculating mixture [18]. For example, the NIBSC supplies 'The 1st International Reference Reagent for Tetanus Toxoid For Flocculation Test' [19] which contains 1000 LF per ampoule. The conversion between IU and Lf systems depends on the particular toxoid preparation.

Where bovine materials are used in the culture of *C.tetani*, they should be obtained from sources that are free from bovine spongiform encephalopathy (BSE) or from other transmissible spongiform encephalopathies (TSEs).

The tetanus toxoid in the immunogenic compositions of the invention is typically present in an amount that is capable of eliciting an immune response when administered. Ideally, tetanus toxoid can elicit a protective immune response. The amount of tetanus toxoid in immunogenic compositions of the invention is typically 1-20 Lf per dose. Booster vaccines for adolescents and adults typically contain 5 Lf of tetanus toxoid per 0.5 ml dose. Paediatric vaccines typically contain between 5 and 10 Lf of tetanus toxoid per 0.5 ml dose.

It will be apparent to one skilled in the art that in some embodiments, tetanus toxoid may be present in both free (unconjugated) and conjugated form or primarily in conjugated form, that is more than 80, 85, 90, 91, 92, 93, 94, 95, 96, 97, 98, 99% of the tetanus toxoid is present in conjugated form. Thus, the amount of tetanus toxoid in immunogenic compositions of the invention may refer to unconjugated tetanus toxoid alone, conjugated tetanus toxoid alone or the sum of unconjugated and conjugated tetanus toxoid. However, preferably the tetanus toxoid is free, unconjugated. In preferred embodiments, the amount of tetanus toxoid in immunogenic compositions of the invention refers to unconjugated tetanus toxoid alone.

The tetanus toxoid may be adsorbed onto an aluminium hydroxide adjuvant, but this is not necessary (e.g. adsorption of between 0-10% of the total tetanus toxoid can be used).

Typically, the immunogenic composition comprising tetanus toxoid is substantially free from any mercurial preservatives.

Acellular Pertussis Antigen(s)

*Bordetella pertussis* is a Gram-negative non-sporing aerobic bacterium that causes whooping cough. As described in more detail in chapter 21 of reference 1, vaccines against *B.pertussis* have been available for many years, and fall into two categories: cellular (wP) and acellular (aP). Cellular vaccines comprise whole *B.pertussis* cells which have been killed and deactivated (e.g. by treatment with formalin and/or heat), whereas acellular vaccines comprise specific purified *B.pertussis* antigens, either purified from the native bacterium or purified after expression in a recombinant host.

The invention may use more than one acellular pertussis (aP) antigen in a single vaccine e.g. at least two or at least three, of the following well-known and well-characterized *B.pertussis* antigens: (1) detoxified pertussis toxin (pertussis toxoid, or 'PT'); (2) filamentous hemagglutinin ('FHA'); (3) pertactin ('PRN', also known as the '69 kiloDalton outer membrane protein' or '69K'). It is most preferred that all three of these antigens should be used. These three antigens are preferably prepared by isolation from *B.pertussis* culture, for example, grown in modified Stainer-Scholte liquid medium. PT and FHA can be isolated from the fermentation broth (e.g. by adsorption on hydroxyapatite gel), whereas pertactin can be extracted from the cells by heat treatment and flocculation (e.g. using barium chloride). The antigens can be purified in successive chromatographic and/or precipitation steps. PT and FHA can be purified by hydrophobic chromatography, affinity chromatography and size exclusion chromatography. Pertactin can be purified by ion exchange chromatography, hydrophobic chromatography and size exclusion chromatography. Methods for purification of PT, FHA and pertactin are known in the art.

FHA and pertactin may be treated with formaldehyde prior to use according to the invention. PT may be detoxified by treatment with formaldehyde and/or glutaraldehyde. As an alternative to this chemical detoxification procedure, in preferred embodiments the PT may be a mutant PT in which enzymatic activity has been reduced by mutagenesis [20] (e.g. the 9K/129G double mutant). When genetically detoxified PT is included, a reduced amount may be used. For example, the concentration of genetically detoxified pertussis toxoid in the composition may be <5 μg/ml e.g. <4, <3, <2.5, <2, <1 μg/ml, etc. In a typical 0.5 ml unit dose volume, therefore, the amount of genetically detoxified pertussis toxoid is less than 2.5 μg e.g. <2, <1.5, <1, <0.5 μg, for example, from about 0.5 μg to about 2.5 μg.

Further acellular pertussis antigens that can be used include fimbriae (e.g. agglutinogens 2 and 3 also referred to as FIM2 and FIM3).

The aP antigen(s) may be used in an unadsorbed state, but they are preferably adsorbed onto one or more aluminium salt adjuvant(s) before being used. The aP antigens are preferably adsorbed onto an aluminium hydroxide adjuvant.

Typically, the immunogenic composition comprising aP antigens are substantially free from mercurial preservatives (e.g. thimerosal).

The acellular pertussis antigen is typically present in the immunogenic compositions of the invention in an amount that is capable of eliciting an immune response when administered. Ideally, the acellular pertussis antigen can elicit a protective immune response. Quantities of acellular pertussis antigens are typically expressed in micrograms. The concentration of PT in a vaccine is usually between 5 and 50 μg/ml. Typical PT concentrations are 5 μg/ml, 16 μg/ml, 20 μg/ml or 50 μg/ml. The concentration of FHA in a vaccine is usually between 10 and 50 μg/ml. Typical FHA concentrations are 10 μg/ml, 16 μg/ml or 50 μg/ml. The concentration of pertactin in a vaccine is usually between 5 and 16 μg/ml. Typical pertactin concentrations are 5 μg/ml, 6 μg/ml or 16 μg/ml. For example, a booster vaccine for adolescents and adults typically contains 2.5 to 8 μg PT, 4 to 8 μg FHA (for example, between 4 and 8 μg FHA) and 2.5 to 8 μg pertactin (for example, between 2.5 and 8 μg pertactin) per 0.5 ml dose. Typically, a booster vaccine comprises 4 μg PT, 4 μg FHA and 8 μg pertactin, more preferably 5 μg PT, 2.5 μg FHA and 2.5 μg pertactin, per 0.5 ml dose. A paediatric vaccine usually comprises 7 μg PT, 10 μg FHA and 10 μg pertactin, per 0.5 ml dose.

Where the aqueous component includes each of PT, FHA and pertactin, their weight ratios can vary, but may be e.g. about 16:16:5, about 5:10:6, about 20:20:3, about 25:25:8, or about 10:5:3 (PT:FHA:PRN).

Specific Immunogenic Compostions of the Invention

Specifically envisaged immunogenic compositions of the invention comprise:

- (i) a *B. pertussis* OMV, (ii) a diphtheria toxoid, (iii) a tetanus toxoid, (iv) acellular pertussis antigen.
- (i) a *B. pertussis* OMV, (ii) a diphtheria toxoid, (iii) a tetanus toxoid, (iv) detoxified pertussis toxin, (v) filamentous hemagglutinin and (vi) pertactin.
- (i) a *B. pertussis* OMV, (ii) a diphtheria toxoid, (iii) a tetanus toxoid, (iv) genetically detoxified pertussis toxoin (v) filamentous hemagglutinin and (vi) pertactin.
- (i) a *B. pertussis* OMV, (ii) a diphtheria toxoid, (iii) a tetanus toxoid, (iv) detoxified pertussis toxin, (v) filamentous hemagglutinin, (vi) pertactin, (vii) an antigen from a poliovirus Type 1 strain, (viii) an antigen from a poliovirus Type 2 strain and (ix) an antigen from a poliovirus Type 3 strain.

Immunogenic compositions of the present invention elicit an enhanced TH1 and an enhanced TH2 response, i.e., an increase in the production of both IgG1 and IgG2a production. More particularly, the compositions elicit an increased TH1 and/or an increased TH2 immune response relative to immunization with OMV alone or TdaP alone.

Pharmaceutical Methods and Uses

The immunogenic compositions of the invention may further comprise a pharmaceutically acceptable carrier. Typical 'pharmaceutically acceptable carriers' include any carrier that does not itself induce the production of antibodies harmful to the individual receiving the composition. Suitable carriers are typically large, slowly metabolised macromolecules such as proteins, polysaccharides, polylactic acids, polyglycolic acids, polymeric amino acids, amino acid copolymers, sucrose [21], trehalose [22], lactose, and lipid aggregates (such as oil droplets or liposomes). Such carriers are well known to those of ordinary skill in the art. The vaccines may also contain diluents, such as water, saline, glycerol, etc. Additionally, auxiliary substances, such as wetting or emulsifying agents, pH buffering substances, and the like, may be present. Sterile pyrogen-free, phosphate-buffered physiologic saline is a typical carrier. A thorough discussion of pharmaceutically acceptable excipients is available in reference 23.

Compositions of the invention may be in aqueous form (i.e. solutions or suspensions) or in a dried form (e.g. lyophilised). If a dried vaccine is used then it will be reconstituted into a liquid medium prior to injection. Lyophilisation of vaccines is known in the art e.g. the Menjugate™ product is presented in lyophilised form. When the immunogenic compositions of the invention include a lyophilised component, it is typical for that component to be prepared separately, mixed and then lyophilised. To stabilise antigens during lyophilisation, non-active components, e.g. as stabilizers, can be added prior to freeze-drying. Preferred stabilizers for inclusion are lactose, sucrose and mannitol, as well as mixtures thereof e.g. lactose/sucrose mixtures, sucrose/mannitol mixtures, etc. A final vaccine obtained by aqueous reconstitution of the lyophilised material may thus contain lactose and/or sucrose. It is preferred to use amorphous excipients and/or amorphous buffers when preparing lyophilised vaccines [24].

It may be preferred to include a sugar alcohol (e.g. mannitol) and/or a disaccharide (e.g. sucrose or trehalose) e.g. at between 1 mg/ml and 30 mg/ml (e.g. about 25 mg/ml) in the composition.

Compositions may be presented in vials, or they may be presented in ready-filled syringes. The syringes may be supplied with or without needles. A syringe will include a single dose of the composition, whereas a vial may include a single dose or multiple doses.

Compositions of the invention are preferably administered to patients in 0.5 ml unit doses. References to 0.5 ml doses will be understood to include normal variance e.g. 0.5 ml±0.05 ml. For multidose situations, multiple dose amounts will be extracted and packaged together in a single container e.g. 5 ml for a 10-dose multidose container (or 5.5 ml with 10% overfill).

Aqueous compositions of the invention are also suitable for reconstituting other vaccines from a lyophilised form. Where a composition of the invention is to be used for such extemporaneous reconstitution, the invention provides a kit, which may comprise two vials, or may comprise one ready-filled syringe and one vial, with the contents of the syringe being used to reactivate the contents of the vial prior to injection.

Vaccines can also be prepared in a form where the vaccine can be prepared extemporaneously at the time/point of use by mixing together two components. Such two-component embodiments include liquid/liquid mixing and liquid/solid mixing e.g. by mixing aqueous material with lyophilised material.

Thus, a kit useful for the invention comprises a first component comprising the OMV component and a second component comprising (a) acellular pertussis antigen(s), (b) a tetanus toxoid, (c) a diphtheria toxoid; wherein the two components are in separate containers (e.g. vials and/or syringes). The OMV component in the first component may be lyophilised. In some embodiments, the first component does not comprise an adjuvant. The second component may comprise aqueous antigens. In some embodiments, the second component comprises an adjuvant, for example, an aluminium salt adjuvant.

The invention also provides a process for preparing the immunogenic composition of the invention, comprising mixing a first component comprising the OMV and a second component comprising (a) acellular pertussis antigen(s), (b) a tetanus toxoid and (c) a diphtheria toxoid. The OMV in the first component may be lyophilised. The second component may comprise aqueous antigens. The process may comprise a further step of reconstituting the lyophilised OMV in the first component with the aqueous antigens of the second component. The first component may not comprise an adjuvant. The second component may comprise an adjuvant, for example, an aluminium salt adjuvant.

Compositions of the invention may be packaged in unit dose form or in multiple dose form. For multiple dose forms, vials are preferred to pre-filled syringes. Effective dosage volumes can be routinely established, but a typical human dose of the composition has a volume of 0.5 ml e.g. for intramuscular injection.

The pH of the composition is preferably between 6 and 8, preferably about 7. Stable pH may be maintained by the use of a buffer. Aqueous compositions administered to a patient can have a pH of between 5.0 and 7.5, and more typically between 5.0 and 6.0 for optimum stability; where a diphtheria toxoid and/or tetanus toxoid is present, the pH is ideally between 6.0 and 7.0.

The immunogenic compositions of the invention typically comprise a potassium dihydrogen phosphate buffer. The potassium dihydrogen phosphate buffer may comprise about 1-10 mM potassium dihydrogen phosphate, e.g. 1.25 mM, 2.5 mM or 5.0 mM. If a composition comprises an aluminium hydroxide salt, it is preferred to use a histidine buffer [25]. The composition may be sterile and/or pyrogen-free. Compositions of the invention may be isotonic with respect to humans.

Compositions of the invention are immunogenic, and are more preferably vaccine compositions. Vaccines according to the invention may either be prophylactic (i.e. to prevent infection) or therapeutic (i.e. to treat infection), but will typically be prophylactic. Prophylactic vaccines do not guarantee complete protection from disease because even if the patient develops antibodies, there may be a lag or delay before the immune system is able to fight off the infection. Therefore, and for the avoidance of doubt, the term prophylactic vaccine may also refer to vaccines that ameliorate the effects of a future infection, for example by reducing the severity or duration of such an infection.

The terms "protection against infection" and/or "provide protective immunity" means that the immune system of a subject has been primed (e.g by vaccination) to trigger an immune response and repel infection. Particularly, the immune response triggered is capable of repelling infection against a number of pathogens, such as different strains of bacteria. A vaccinated subject may thus get infected, but is better able to repel the infection than a control subject. Immunogenic compositions used as vaccines comprise an immunologically effective amount of antigen(s), as well as any other components, as needed. By 'immunologically effective amount', it is meant that the administration of that amount to an individual, either in a single dose or as part of a series, is effective for treatment or prevention. Commonly, the desired result is the production of an antigen (e.g., pathogen)-specific immune response that is capable of or contributes to protecting the subject against the pathogen. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials.

The compositions of the invention may be prepared in various forms. For example, the compositions may be prepared as injectables, either as liquid solutions or suspensions. The composition may be prepared for pulmonary administration e.g. as an inhaler, using a fine powder or a spray. The composition may be prepared as a suppository or pessary. The composition may be prepared for nasal, aural or ocular administration e.g. as spray, drops, gel or powder [e.g. refs 26 & 27]. Success with nasal administration of pneumococcal saccharides [28,29], Hib saccharides [30], MenC saccharides [31], and mixtures of Hib and MenC saccharide conjugates [32] has been reported.

Compositions of the invention may include an antimicrobial, particularly when packaged in multiple dose format.

Compositions of the invention may comprise detergent e.g. a Tween (polysorbate), such as Tween 80. Detergents are generally present at low levels e.g. <0.01%.

Compositions of the invention may include sodium salts (e.g. sodium chloride) to give tonicity. A concentration of 10±2 mg/ml NaCl is typical. In some embodiments, a concentration of 4-10 mg/ml NaCl may be used, e.g. 9.0, 7.0, 6.75 or 4.5 mg/ml.

Compositions will generally have an osmolality of between 200 mOsm/kg and 400 mOsm/kg, preferably between 240-360 mOsm/kg, and will more preferably fall within the range of 280-320 mOsm/kg. Osmolality has previously been reported not to have an impact on pain caused by vaccination [33], but keeping osmolality in this range is nevertheless preferred.

Compositions of the invention will generally include a buffer. A phosphate buffer is typical.

Compositions of the invention may be administered in conjunction with other immunoregulatory agents. In particular, compositions may include one or more adjuvants. Such adjuvants include, but are not limited to mineral-containing compositions.

Mineral containing compositions suitable for use as adjuvants in the invention include mineral salts, such as aluminium salts and calcium salts (or mixtures thereof). Calcium salts include calcium phosphate (e.g. the "CAP" particles disclosed in ref. 34). Aluminium salts include hydroxides, phosphates, sulfates, etc., with the salts taking any suitable form (e.g. gel, crystalline, amorphous, etc.). Adsorption to these salts is preferred. The mineral containing compositions may also be formulated as a particle of metal salt [35].

The adjuvants known as aluminium hydroxide and aluminium phosphate may be used. These names are conventional, but are used for convenience only, as neither is a precise description of the actual chemical compound which is present (e.g. see chapter 9 of reference 36). The invention can use any of the "hydroxide" or "phosphate" adjuvants that are in general use as adjuvants. The adjuvants known as "aluminium hydroxide" are typically aluminium oxyhydroxide salts, which are usually at least partially crystalline. The adjuvants known as "aluminium phosphate" are typically aluminium hydroxyphosphates, often also containing a small amount of sulfate (i.e. aluminium hydroxyphosphate sulfate). They may be obtained by precipitation, and the reaction conditions and concentrations during precipitation influence the degree of substitution of phosphate for hydroxyl in the salt.

A fibrous morphology (e.g. as seen in transmission electron micrographs) is typical for aluminium hydroxide adjuvants. The pI of aluminium hydroxide adjuvants is typically about 11 i.e. the adjuvant itself has a positive surface charge at physiological pH. Adsorptive capacities of between 1.8-2.6 mg protein per mg $Al^{+++}$ at pH 7.4 have been reported for aluminium hydroxide adjuvants.

Aluminium phosphate adjuvants generally have a $PO_4$/Al molar ratio between 0.3 and 1.2, preferably between 0.8 and 1.2, and more preferably 0.95±0.1. The aluminium phosphate will generally be amorphous, particularly for hydroxyphosphate salts. A typical adjuvant is amorphous aluminium hydroxyphosphate with $PO_4$/Al molar ratio between 0.84 and 0.92, included at 0.6 mg $Al^{3+}$/ml. The aluminium phosphate will generally be particulate (e.g. plate-like morphology as seen in transmission electron micrographs). Typical diameters of the particles are in the range 0.5-20 μm (e.g. about 5-10 μm) after any antigen adsorption. Adsorptive capacities of between 0.7-1.5 mg protein per mg $Al^{+++}$ at pH 7.4 have been reported for aluminium phosphate adjuvants.

The point of zero charge (PZC) of aluminium phosphate is inversely related to the degree of substitution of phosphate for hydroxyl, and this degree of substitution can vary depending on reaction conditions and concentration of reactants used for preparing the salt by precipitation. PZC is also altered by changing the concentration of free phosphate ions in solution (more phosphate=more acidic PZC) or by adding a buffer such as a histidine buffer (makes PZC more basic). Aluminium phosphates used according to the invention will generally have a PZC of between 4.0 and 7.0, more preferably between 5.0 and 6.5 e.g. about 5.7.

Suspensions of aluminium salts used to prepare compositions of the invention may contain a buffer (e.g. a phosphate or a histidine or a Tris buffer), but this is not always necessary. The suspensions are preferably sterile and pyrogen-free. A suspension may include free aqueous phosphate ions e.g. present at a concentration between 1.0 and 20 mM, preferably between 5 and 15 mM, and more preferably about 10 mM. The suspensions may also comprise sodium chloride.

The invention can use a mixture of both an aluminium hydroxide and an aluminium phosphate. In this case there may be more aluminium phosphate than hydroxide e.g. a weight ratio of at least 2:1 e.g. ≥5:1, ≥6:1, ≥7:1, ≥8:1, ≥9:1, etc.

The concentration of $Al^{+++}$ in a composition for administration to a patient is preferably less than 10 mg/ml e.g. ≤5 mg/ml, ≤4 mg/ml, ≤3 mg/ml, ≤2 mg/ml, ≤1 mg/ml, etc. A preferred range is between 0.3 and 1 mg/ml. A maximum of 0.85 mg/dose is preferred.

A typical adjuvant aluminium phosphate adjuvant is amorphous aluminium hydroxyphosphate with $PO_4$/Al molar ratio between 0.84 and 0.92, included at 0.6 mg $Al^{3+}$/ml. Adsorption with a low dose of aluminium phosphate may be used e.g. between 50 and 100 μg $Al^{3+}$ per dose.

The use of aluminium salt adjuvants is particularly preferred, and antigens are generally adsorbed to such salts. It is possible in compositions of the invention to adsorb some antigens to an aluminium hydroxide but to have other antigens in association with an aluminium phosphate. In general, however, it is preferred to use only a single salt e.g. a hydroxide or a phosphate, but not both. Not all antigens need to be adsorbed i.e. some or all can be free in solution.

Methods of Treatment

The invention also provides immunogenic compositions for use in raising an immune response in a mammal, comprising administering an immunogenic composition of the invention to the mammal. The immunogenic composition is preferably able to raise an immune response in a mammal. The immune response is preferably protective and preferably involves antibodies. and is more preferably a vaccine. In some embodiments the vaccine is for use in primary vaccination. The immunogenic composition may raise a booster response. Compositions of the invention are preferably administered to patients in 0.5 ml doses (as discussed above).

The invention also provides a method for raising an immune response in a mammal, comprising administering an immunogenic composition of the invention to the mammal. The immune response is preferably protective and preferably involves antibodies. The method may raise a booster response. Compositions of the invention are preferably administered to patients in 0.5 ml doses (as discussed above).

The mammal is preferably a human. Where the vaccine is for prophylactic use, the human is preferably a child (e.g. a toddler or infant, particularly a neonate) or a teenager. A vaccine intended for children may also be administered to adults e.g. to assess safety, dosage, immunogenicity, etc. A preferred class of humans for treatment are females of child-bearing age (e.g. teenagers and above). Another preferred class is pregnant females.

In some embodiments, the patient has been pre-immunised with a diphtheria toxoid or derivative thereof. In other embodiments, the patient has been pre-immunised with a tetanus toxoid or derivative thereof. In some embodiments, the patient has been pre-immunised with both a diphtheria toxoid or derivative thereof and a tetanus toxoid or derivative thereof.

The invention also provides a composition of the invention for use as a medicament.

The invention also provides the use of a composition of the invention in the manufacture of a medicament for raising an immune response in a mammal.

These uses and methods are preferably for the prevention and/or treatment of a disease caused by one or more of *Corynebacterium diphtheriae, Clostridium tetani* and *Bordetella pertussis. C.diphtheria* can cause diphtheria; *C.tetani* can cause tetanus; *B.pertussis* can cause whooping cough.

The subject in which disease is prevented may not be the same as the subject that receives the immunogenic composition of the invention. For instance, an immunogenic composition may be administered to a female (before or during pregnancy) in order to protect offspring (so-called 'maternal immunization' [37-39]). The immunization of the pregnant female provides antibody-mediated immunity to the infant through passive maternal immunity. The passive immunity occurs naturally when maternal antibodies are transferred to the fetus through the placenta. Passive immunity is especially important to infants because they are born without any actively acquired immunity. Administration of compositions of the invention to a pregnant female enhances immunity in the female, and antibodies are passed to the newborn through the placenta, conferring passive maternal immunity on the infant. However, passive immunity in infants is only temporary and starts to decrease after the first few weeks, or months of life. As passive immunity is only temporary, it may be important for the infant to receive administration of a composition of the invention, to induce active immunity in the infant, before the passive immunity diminishes. Administration of a second immunogenic composition to the infant after birth induces active immunity in the infant, and extends the immunity passed on from the mother during pregnancy.

As used herein, an infant is an individual under one year of age (e.g., less than one day old, 1 week old, 2 weeks old, 3 weeks old, 4 weeks old, 2 months old, 3 months, 4 months, 5 months, 6 months, 7 months, 8 months old, 9 months old, 10 months old, 11 months old, less than 12 months old).

The pregnant female may be administered the composition of the invention at any time during her pregnancy. For example, the composition may be administered to the female during the first, second or third trimester of her pregnancy. In some embodiments, the composition is administered to the female during the last 6-12 weeks of the pregnancy (e.g., 28 weeks gestation, 29 weeks gestation, 30 weeks gestation, 31 weeks gestation, 32 weeks gestation, 33 weeks gestation, 34 weeks gestation, 35 weeks gestation, 36 weeks gestation, 37 weeks gestation, 38 weeks gestation, 39 weeks gestation). Particularly, the composition of the invention is administered to the pregnant female at least four weeks before delivery of the infant. In some embodiments, a one-dose regimen is administered to the pregnant female between weeks 32 and 36 gestation. In other embodiments, a two-dose regimen is administered to the pregnant female, with the first dose being administered at approximately 32 weeks gestation and the second dose being administered at approximately 36 weeks gestation.

The infant may be administered the composition at any time during the first year of life, and thereafter if desired. Generally the composition will be administered to the infant one, two, three, four or more times during the first year of life. For example, the composition of the invention may be administered to the infant one or more times selected from at birth, at 2 weeks old, 4 weeks old, 6 weeks old, 2 months old, 3 months old, 4 months old, 6 months old, 9 months old, and 12 months old. Particularly, the composition of the invention is administered to the infant at a time before maternal antibodies have decreased to non-protective titers. Subsequent administrations can occur on any desired schedule.

In one embodiment, there is provided a method of protecting an infant against a disease caused by one or more of *Corynebacterium diphtheriae. Clostridium tetani* and *Bordetella pertussis* comprising the steps of (a) administering a composition of the invention to a female during pregnancy with said infant; and (b) optionally administering a composition of the invention to the infant that is born from the pregnancy.

Thus, there is also provided a method of protecting an infant against one or more of diphtheria, tetanus and whooping cough comprising the steps of (a) administering a composition of the invention to a female during pregnancy with said infant; and (b) optionally administering a composition of the invention to the infant that is born from the pregnancy.

Preferred compositions of the invention can confer an antibody titre in a patient that is superior to the criterion for seroprotection for each antigenic component for an acceptable percentage of human subjects. Antigens with an associated antibody titre above which a host is considered to be seroconverted against the antigen are well known, and such titres are published by organisations such as WHO. Preferably more than 80% of a statistically significant sample of subjects is seroconverted, more preferably more than 90%, still more preferably more than 93% and most preferably 96-100%.

Compositions of the invention will generally be administered directly to a patient. Direct delivery may be accomplished by parenteral injection (e.g. subcutaneously, intraperitoneally, intravenously, intramuscularly, or to the interstitial space of a tissue), or by rectal, oral, vaginal, topical, transdermal, intranasal, ocular, aural, pulmonary or other mucosal administration. Intramuscular administration to the thigh or the upper arm is preferred. Injection may be via a needle (e.g. a hypodermic needle), but needle-free injection may alternatively be used. A typical intramuscular dose is 0.5 ml.

The invention may be used to elicit systemic and/or mucosal immunity.

The immunogenic compositions of the invention may be administered in single or multiple doses. Administration of a single dose is preferred in the invention. Alternatively, a further one unit dose followed by a first unit dose may be effective. Typically, the second (or third, fourth, fifth etc.) unit dose is identical to the first unit dose. Typically, the immunogenic compositions of the invention are administered in three unit doses. Typically, the immunogenic compositions of the invention will be administered intramuscularly, e.g. by intramuscular administration to the thigh or the upper arm.

Multiple doses may be used in a primary immunization schedule and/or in a booster immunization schedule. A primary dose schedule may be followed by a booster dose schedule. Suitable timing between priming doses (e.g. between 4-16 weeks), and between priming and boosting, can be routinely determined.

In order to have full efficacy, a typical primary immunization schedule (particularly for a child) may involve administering more than one dose. For example, doses may be at: 0 & 6 months (time 0 being the first dose); at 0, 1, 2 & 6 months; at day 0, day 21 and then a third dose between 6 & 12 months; at 2, 4 & 6 months; at 3, 4 & 5 months; at 6, 10 & 14 weeks; at 2, 3 & 4 months; or at 0, 1, 2, 6 & 12 months. Paediatric compositions can also be used as booster doses e.g. for children, in the second year of life.

Compositions can also be used as booster doses e.g. for children, in the second year of life. Adolescent booster vaccine compositions of the invention are administered in a single dose to persons of age 10 and older. The immunogenic composition of the invention can be administered as a booster vaccine to a patient who has previously been vaccinated against both diphtheria and tetanus, and preferably also against pertussis. These patients can be distinguished from the general population by having an immunological memory response against the previous vaccine. The patients may have received their most recent diphtheria and/or tetanus vaccines at least five years before receiving the vaccine of the invention. The patients receiving the vaccines may be aged between 4 and 65 years of age e.g. 11-64 years, 10-18 years, etc.

Any suitable route of administration can be used. For example, a composition can be administered intramuscularly, intraperitoneally, subcutaneously, transdermally, or intradermally. If desired, the composition can be administered through an intramucosal route such as intra-orally, intra-nasally, intra-vaginally, and intra-rectally. Administration to the pregnant female and the infant may be through the same route or different routes. Compositions of the invention can be administered by intramuscular injection e.g. into the arm or leg.

Vaccines produced by the invention may be administered to patients at the same time as a separate vaccine, e.g. at the same time as a pneumococcal conjugate vaccine such as PREVNAR™, at the same time as an influenza vaccine, at the same time as a rotavirus vaccine, at the same time as a MMR vaccine, etc.

Where compositions of the invention include an aluminium-based adjuvant, settling of components may occur during storage. The composition should therefore be shaken prior to administration to a patient. The shaken composition will be a turbid white suspension.

EMBODIMENTS

Embodiment 1. An immunogenic composition comprising (a) an Outer Membrane Vesicle (OMV), (b) an acellular pertussis antigen, (c) a tetanus toxoid and (d) a diphtheria toxoid, wherein the OMV is derived from *Bordetella pertussis.*

Embodiment 2. An immunogenic composition comprising (a) a *Bordetella pertussis* Outer Membrane Vesicle (OMV), (b) an acellular pertussis antigen, (c) a tetanus toxoid and (d) a diphtheria toxoid.

Embodiment 3. The immunogenic composition according to Embodiment 1 or Embodiment 2, wherein the acellular pertussis antigen is selected from the group consisting of (i) detoxified pertussis toxin (PT), (ii) filamentous hemagglutinin (FHA) and (iii) pertactin (PRN).

Embodiment 4. The immunogenic composition according to Embodiment 3, wherein the acellular pertussis antigen comprises PT, FHA and PRN.

Embodiment 5. The immunogenic composition according to Embodiment 4, wherein PT, FHA and PRN are present at a ratio of 16:16:5 (measured by weight).

Embodiment 6. The immunogenic composition according to any one of the preceding Embodiments, wherein the diphtheria toxoid is present at a concentration of between 4 Lf/ml and 8 Lf/ml, for example, 4 Lf per 0.5 ml dose.

Embodiment 7. The immunogenic composition according to any one of Embodiments 1 to 6, wherein the diphtheria toxoid is present at a concentration of between 20 and 50 Lf/ml, for example, 25 Lf per 0.5 ml dose.

Embodiment 8. The immunogenic composition according to any one of the preceding Embodiments, wherein tetanus toxoid is present at a concentration of about 5 Lf per 0.5 ml dose.

Embodiment 9. The immunogenic composition according to any one of Embodiments 1 to 8, wherein tetanus toxoid is present at a concentration of between 5 and 10 Lf per 0.5 ml dose.

Embodiment 10. The immunogenic composition according to any one of Embodiments 1 to 9, wherein the diphtheria toxoid and tetanus toxoid are present at a diphtheria toxoid:tetanus toxoid ratio that is greater than 1, for example, between 2:1 and 3:1 (measured in Lf units), such as 2.5:1.

Embodiment 11. The immunogenic composition according to any one of Embodiments 1 to 9, wherein the diphtheria toxoid and tetanus toxoid are present at a tetanus toxoid:diphtheria toxoid ratio that is greater than 1, for example, between 1.5:1 and 2.5:1 (measured in Lf units), such as 2:1.

Embodiment 12. The immunogenic composition according to any one of the preceding Embodiments, wherein the immunogenic composition contains an adjuvant.

Embodiment 13. The immunogenic composition according to any one of the preceding Embodiments, wherein the immunogenic composition contains an aluminium salt adjuvant.

Embodiment 14. The immunogenic composition according to any one of the preceding Embodiments, wherein the composition is an injectable liquid solution or suspension.

Embodiment 15. The immunogenic composition according to any one of Embodiments 1 to 14, wherein the composition is lyophilised.

Embodiment 16. The immunogenic compositions according to any one of the preceding Embodiments, wherein the composition is preservative-free.

Embodiment 17. The immunogenic composition according to any one of the preceding Embodiments, wherein the composition is a vaccine.

Embodiment 18. The immunogenic composition according to any one of the preceding Embodiments, wherein the composition is for administration to a human.

Embodiment 19. The immunogenic composition according to any one of the preceding Embodiments, wherein the composition is for use as a medicament.

Embodiment 20. A method for raising an immune response in a patient, comprising the step of administering to the patient a composition according to any one of the preceding Embodiments.

Embodiment 21. A method for raising an immune response in a patient, comprising the step of administering to the patient a composition comprising (a) a *Bordetella pertussis* Outer Membrane Vesicle (OMV), (b) an acellular pertussis antigen, (c) a tetanus toxoid and (d) a diphtheria toxoid.

Embodiment 22. A process for preparing the immunogenic composition according to any one of Embodiments 1-19, comprising mixing a first component comprising the Outer Membrane Vesicle (OMV) and a second component comprising the acellular pertussis antigen, the tetanus toxoid and the diphtheria toxoid.

Embodiment 23. The process according to Embodiment 22, wherein the OMV in the first component is lyophilised.

Embodiment 24. The process according to Embodiment 22 or Embodiment 23, wherein the second component comprises aqueous antigens.

Embodiment 25. The process according to Embodiment 24, comprising a further step of reconstituting the lyophilised OMV in the first component with the aqueous antigens of the second component.

Embodiment 26. The process according to any one of Embodiments 22 to 25, wherein the first component does not comprise an adjuvant.

Embodiment 27. The process according to any of one Embodiments 22 to 26, wherein the second component comprises an adjuvant, for example, an aluminium salt adjuvant.

Embodiment 28. A kit for preparing the immunogenic composition according to any one of Embodiments 1-19, comprising a first component comprising the OMV and a second component comprising the acellular pertussis antigen, the tetanus toxoid and the diphtheria toxoid, wherein the two components are in separate containers.

Embodiment 29. The kit of Embodiment 28, wherein the OMV in the first component is lyophilised.

Embodiment 30. The kit according to Embodiment 28 or Embodiment 29, wherein the second component comprises aqueous antigens.

Embodiment 31. The kit according to any one of Embodiments 28-30, wherein the first component does not comprise an adjuvant.

Embodiment 32. The kit according to any of one Embodiments 28-31, wherein the second component comprises an adjuvant, for example, an aluminium salt adjuvant.

Embodiment 33. An immunogenic composition comprising (a) Outer Membrane Vesicles (OMVs), (b) an acellular pertussis antigen, (c) a tetanus toxoid and (d) a diphtheria toxoid, wherein the OMVs are derived from a *Bordetella pertussis* strain expressing a genetically detoxified pertussis toxoid, particularly the genetically detoxified pertussis toxoid PT 9K/129G.

Embodiment 34. An immunogenic composition comprising (a) Outer Membrane Vesicles (OMVs), (b) an acellular pertussis antigen, (c) a tetanus toxoid and (d) a diphtheria toxoid, wherein the OMVs are derived from a *Bordetella pertussis* strain expressing the genetically detoxified pertussis toxoid PT 9K/129G.

Embodiment 35. An immunogenic composition comprising (a) Outer Membrane Vesicles (OMVs), (b) an acellular pertussis antigen, (c) a tetanus toxoid and (d) a diphtheria toxoid, wherein the OMVs are derived from a *Bordetella pertussis* strain that comprises an S1 gene which has been modified to include the mutations R9K and E129G and which expresses the genetically detoxified pertussis toxoid PT-9K/129G.

Embodiment 36. An immunogenic composition comprising (a) Outer Membrane Vesicles (OMVs), (b) an acellular pertussis antigen, (c) a tetanus toxoid and (d) a diphtheria toxoid, wherein the OMVs are derived from a *Bordetella pertussis* strain that comprises an S1 gene which has been modified to include the mutations R9K and E129G and which expresses the genetically detoxified pertussis toxoid PT-9K/129G and wherein the OMVs are not chemically detoxified.

Embodiment 37. An immunogenic composition comprising (a) Outer Membrane Vesicles (OMVs), (b) an acellular pertussis antigen, (c) a tetanus toxoid and (d) a diphtheria toxoid, wherein the OMVs are derived from a *Bordetella pertussis* strain that comprises an S1 gene which has been modified to include the mutations R9K and E129G and which expresses the genetically detoxified pertussis toxoid PT-9K/129G and wherein the OMVs are not chemically detoxified and/or treated with formaldehyde, formalin, glutaraldehyde, hydrogen peroxide and combinations or derivatives thereof.

Embodiment 38. An immunogenic composition comprising (a) Outer Membrane Vesicles (OMVs), (b) an acellular pertussis antigen, (c) a tetanus toxoid and (d) a diphtheria toxoid, wherein the OMVs are derived from a *Bordetella pertussis* strain that comprises an S1 gene which has been modified to include the mutations R9K and E129G and which expresses the genetically detoxified pertussis toxoid PT-9K/129G and wherein the Lipid A in the OMVs has a modified structure without glucosamine (GlcN) substitutions on the distal phosphate groups of the core structure.

Embodiment 39. An immunogenic composition comprising (a) Outer Membrane Vesicles (OMVs), (b) an acellular pertussis antigen, (c) a tetanus toxoid and (d) a diphtheria toxoid, wherein the OMVs are derived from a *Bordetella pertussis* strain that comprises an S1 gene which has been modified to include the mutations R9K and E129G and which expresses the genetically detoxified pertussis toxoid PT-9K/129G, wherein the Lipid A in the OMVs has a modified structure without glucosamine (GlcN) substitutions on the distal phosphate groups of the core structure and wherein the OMVs are not chemically detoxified and/or treated with formaldehyde, formalin, glutaraldehyde, hydrogen peroxide and combinations or derivatives thereof.

Embodiment 40. An immunogenic composition comprising (a) Outer Membrane Vesicles (OMVs), (b) an acellular pertussis antigen selected from the group consisting of (i) detoxified pertussis toxin (PT), (ii) filamentous hemagglutinin (FHA) and (iii) pertactin (PRN), (c) a tetanus toxoid and (d) a diphtheria toxoid, wherein the OMVs are derived from a *Bordetella pertussis* strain that comprises an S1 gene which has been modified to include the mutations R9K and E129G and which expresses the genetically detoxified pertussis toxoid PT-9K/129G.

Embodiment 41. An immunogenic composition comprising (a) Outer Membrane Vesicles (OMVs), (b) an acellular pertussis antigen selected from the group consisting of (i) detoxified pertussis toxin (PT), (ii) filamentous hemagglutinin (FHA) and (iii) pertactin (PRN), (c) a tetanus toxoid and (d) a diphtheria toxoid, wherein the OMVs are derived from a *Bordetella pertussis* strain that comprises an S1 gene which has been modified to include the mutations R9K and E129G and which expresses the genetically detoxified pertussis toxoid PT-9K/129G, wherein the Lipid A in the OMVs has a modified structure without glucosamine (GlcN) substitutions on the distal phosphate groups of the core structure and wherein the OMVs are not chemically detoxified.

Embodiment 42. An immunogenic composition comprising (a) Outer Membrane Vesicles (OMVs), (b) an acellular pertussis antigen selected from the group consisting of (i) detoxified pertussis toxin (PT), (ii) filamentous hemagglutinin (FHA) and (iii) pertactin (PRN), (c) a tetanus toxoid and (d) a diphtheria toxoid, wherein the OMVs are derived from a *Bordetella pertussis* strain that comprises an S1 gene which has been modified to include the mutations R9K and E129G and which expresses the genetically detoxified pertussis toxoid PT-9K/129G, wherein the Lipid A in the OMVs has a modified structure without glucosamine (GlcN) substitutions on the distal phosphate groups of the core structure and wherein the OMVs are not chemically detoxified and/or treated with formaldehyde, formalin, glutaraldehyde, hydrogen peroxide and combinations or derivatives thereof.

Embodiment 43. An immunogenic composition comprising (a) Outer Membrane Vesicles (OMVs), (b) (i) detoxified pertussis toxin (PT), (ii) filamentous hemagglutinin (FHA) and (iii) pertactin (PRN), (c) a tetanus toxoid and (d) a diphtheria toxoid, wherein the OMVs are derived from a *Bordetella pertussis* strain that comprises an S1 gene which has been modified to include the mutations R9K and E129G and which expresses the genetically detoxified pertussis toxoid PT-9K/129G.

Embodiment 44. An immunogenic composition comprising (a) Outer Membrane Vesicles (OMVs), (b) (i) detoxified pertussis toxin (PT), (ii) filamentous hemagglutinin (FHA) and (iii) pertactin (PRN), (c) a tetanus toxoid and (d) a diphtheria toxoid, wherein the OMVs are derived from a *Bordetella pertussis* strain that comprises an S1 gene which has been modified to include the mutations R9K and E129G and which expresses the genetically detoxified pertussis toxoid PT-9K/129G, wherein the Lipid A in the OMVs has a modified structure without glucosamine (GlcN) substitutions on the distal phosphate groups of the core structure and wherein the OMVs are not chemically detoxified.

Embodiment 45. An immunogenic composition comprising (a) Outer Membrane Vesicles (OMVs), (b) (i) detoxified pertussis toxin (PT), (ii) filamentous hemagglutinin (FHA) and (iii) pertactin (PRN), (c) a tetanus toxoid and (d) a diphtheria toxoid, wherein the OMVs are derived from a *Bordetella pertussis* strain that comprises an S1 gene which has been modified to include the mutations R9K and E129G and which expresses the genetically detoxified pertussis toxoid PT-9K/129G, wherein the Lipid A in the OMVs has a modified structure without glucosamine (GlcN) substitutions on the distal phosphate groups of the core structure and wherein the OMVs are not chemically detoxified and/or treated with formaldehyde, formalin, glutaraldehyde, hydrogen peroxide and combinations or derivatives thereof.

Embodiment 46. An immunogenic composition comprising (a) *Bordetella pertussis* Outer Membrane Vesicles (OMVs), (b) an acellular pertussis antigen, (c) a tetanus toxoid and (d) a diphtheria toxoid, wherein the OMVs are derived from a *Bordetella pertussis* strain expressing a genetically detoxified pertussis toxoid, particularly the genetically detoxified pertussis toxoid PT 9K/129G.

Embodiment 47. An immunogenic composition comprising (a) *Bordetella pertussis* Outer Membrane Vesicles (OMVs), (b) an acellular pertussis antigen, (c) a tetanus toxoid and (d) a diphtheria toxoid, wherein the OMVs are derived from a *Bordetella pertussis* strain expressing the genetically detoxified pertussis toxoid PT 9K/129G.

Embodiment 48. An immunogenic composition comprising (a) *Bordetella pertussis* Outer Membrane Vesicles (OMVs), (b) an acellular pertussis antigen, (c) a tetanus toxoid and (d) a diphtheria toxoid, wherein the OMVs are derived from a *Bordetella pertussis* strain that comprises an S1 gene which has been modified to include the mutations R9K and E129G and which expresses the genetically detoxified pertussis toxoid PT-9K/129G.

Embodiment 49. An immunogenic composition comprising (a) *Bordetella pertussis* Outer Membrane Vesicles (OMVs), (b) an acellular pertussis antigen, (c) a tetanus toxoid and (d) a diphtheria toxoid, wherein the OMVs are derived from a *Bordetella pertussis* strain that comprises an S1 gene which has been modified to include the mutations R9K and E129G and which expresses the genetically detoxified pertussis toxoid PT-9K/129G and wherein the OMVs are not chemically detoxified.

Embodiment 50. An immunogenic composition comprising (a) *Bordetella pertussis* Outer Membrane Vesicles (OMVs), (b) an acellular pertussis antigen, (c) a tetanus toxoid and (d) a diphtheria toxoid, wherein the OMVs are derived from a *Bordetella pertussis* strain that comprises an S1 gene which has been modified to include the mutations R9K and E129G and which expresses the genetically detoxified pertussis toxoid PT-9K/129G and wherein the OMVs are not chemically detoxified and/or treated with formaldehyde, formalin, glutaraldehyde, hydrogen peroxide and combinations or derivatives thereof.

Embodiment 51. An immunogenic composition comprising (a) *Bordetella pertussis* Outer Membrane Vesicles (OMVs), (b) an acellular pertussis antigen, (c) a tetanus toxoid and (d) a diphtheria toxoid, wherein the OMVs are derived from a *Bordetella pertussis* strain that comprises an S1 gene which has been modified to include the mutations R9K and E129G and which expresses the genetically detoxified pertussis toxoid PT-9K/129G, and wherein the Lipid A in the OMVs has a modified structure without glucosamine (GlcN) substitutions on the distal phosphate groups of the core structure.

Embodiment 52. An immunogenic composition comprising (a) *Bordetella pertussis* Outer Membrane Vesicles (OMVs), (b) an acellular pertussis antigen, (c) a tetanus toxoid and (d) a diphtheria toxoid, wherein the OMVs are derived from a *Bordetella pertussis* strain that comprises an S1 gene which has been modified to include the mutations R9K and E129G and which expresses the genetically detoxified pertussis toxoid PT-9K/129G, and in which the ArnT gene has been knocked-out or deleted, wherein the Lipid A in the OMVs has a modified structure without glucosamine (GlcN) substitutions on the distal phosphate groups of the core structure.

Embodiment 53. An immunogenic composition comprising (a) *Bordetella pertussis* Outer Membrane Vesicles (OMVs), (b) an acellular pertussis antigen, (c) a tetanus toxoid and (d) a diphtheria toxoid, wherein the OMVs are derived from a *Bordetella pertussis* strain that comprises an S1 gene which has been modified to include the mutations R9K and E129G and which expresses the genetically detoxified pertussis toxoid PT-9K/129G, wherein the Lipid A in the OMVs has a modified structure without glucosamine (GlcN) substitutions on the distal phosphate groups of the core structure and wherein the OMVs are not chemically detoxified and/or treated with formaldehyde, formalin, glutaraldehyde, hydrogen peroxide and combinations or derivatives thereof.

Embodiment 54. An immunogenic composition comprising (a) *Bordetella pertussis* Outer Membrane Vesicles (OMVs), (b) an acellular pertussis antigen, (c) a tetanus toxoid and (d) a diphtheria toxoid, wherein the OMVs are derived from a *Bordetella pertussis* strain that comprises an S1 gene which has been modified to include the mutations R9K and E129G and which expresses the genetically detoxified pertussis toxoid PT-9K/129G, and in which the ArnT gene has been knocked-out or deleted, wherein the Lipid A in the OMVs has a modified structure without glucosamine (GlcN) substitutions on the distal phosphate groups of the core structure and wherein the OMVs are not chemically detoxified and/or treated with formaldehyde, formalin, glutaraldehyde, hydrogen peroxide and combinations or derivatives thereof.

Embodiment 55. An immunogenic composition comprising (a) *Bordetella pertussis* Outer Membrane Vesicles (OMVs), (b) an acellular pertussis antigen selected from the group consisting of (i) detoxified pertussis toxin (PT), (ii) filamentous hemagglutinin (FHA) and (iii) pertactin (PRN), (c) a tetanus toxoid and (d) a diphtheria toxoid, wherein the OMVs are derived from a *Bordetella pertussis* strain that comprises an S1 gene which has been modified to include the mutations R9K and E129G and which expresses the genetically detoxified pertussis toxoid PT-9K/129G.

Embodiment 56. An immunogenic composition comprising (a) *Bordetella pertussis* Outer Membrane Vesicles (OMVs), (b) an acellular pertussis antigen selected from the group consisting of (i) detoxified pertussis toxin (PT), (ii) filamentous hemagglutinin (FHA) and (iii) pertactin (PRN), (c) a tetanus toxoid and (d) a diphtheria toxoid, wherein the OMVs are derived from a *Bordetella pertussis* strain that comprises an S1 gene which has been modified to include the mutations R9K and E129G and which expresses the genetically detoxified pertussis toxoid PT-9K/129G, wherein the Lipid A in the OMVs has a modified structure without glucosamine (GlcN) substitutions on the distal phosphate groups of the core structure and wherein the OMVs are not chemically detoxified.

Embodiment 57. An immunogenic composition comprising (a) *Bordetella pertussis* Outer Membrane Vesicles (OMVs), (b) an acellular pertussis antigen selected from the group consisting of (i) detoxified pertussis toxin (PT), (ii) filamentous hemagglutinin (FHA) and (iii) pertactin (PRN), (c) a tetanus toxoid and (d) a diphtheria toxoid, wherein the OMVs are derived from a *Bordetella pertussis* strain that comprises an S1 gene which has been modified to include the mutations R9K and E129G and in which the ArnT gene has been knocked-out or deleted, and which expresses the genetically detoxified pertussis toxoid PT-9K/129G, wherein the Lipid A in the OMVs has a modified structure without glucosamine (GlcN) substitutions on the distal phosphate groups of the core structure and wherein the OMVs are not chemically detoxified and/or treated with formaldehyde, formalin, glutaraldehyde, hydrogen peroxide and combinations or derivatives thereof.

Embodiment 58. An immunogenic composition comprising (a) *Bordetella pertussis* Outer Membrane Vesicles (OMVs), (b) (i) detoxified pertussis toxin (PT), (ii) filamentous hemagglutinin (FHA) and (iii) pertactin (PRN), (c) a tetanus toxoid and (d) a diphtheria toxoid, wherein the OMVs are derived from a *Bordetella pertussis* strain that comprises an S1 gene which has been modified to include the mutations R9K and E129G and which expresses the genetically detoxified pertussis toxoid PT-9K/129G.

Embodiment 59. An immunogenic composition comprising (a) *Bordetella pertussis* Outer Membrane Vesicles (OMVs), (b) (i) detoxified pertussis toxin (PT), (ii) filamentous hemagglutinin (FHA) and (iii) pertactin (PRN), (c) a tetanus toxoid and (d) a diphtheria toxoid, wherein the OMVs are derived from a *Bordetella pertussis* strain that comprises an S1 gene which has been modified to include the mutations R9K and E129G and which expresses the genetically detoxified pertussis toxoid PT-9K/129G, wherein the Lipid A in the OMVs has a modified structure without glucosamine (GlcN) substitutions on the distal phosphate groups of the core structure and wherein the OMVs are not chemically detoxified.

Embodiment 60. An immunogenic composition comprising (a) *Bordetella pertussis* Outer Membrane Vesicles (OMVs), (b) (i) detoxified pertussis toxin (PT), (ii) filamentous hemagglutinin (FHA) and (iii) pertactin (PRN), (c) a tetanus toxoid and (d) a diphtheria toxoid, wherein the OMVs are derived from a *Bordetella pertussis* strain that comprises an S1 gene which has been modified to include the mutations R9K and E129G and which expresses the genetically detoxified pertussis toxoid PT-9K/129G, and in which the AmT gene has been knocked-out or deleted, wherein the Lipid A in the OMVs has a modified structure without glucosamine (GlcN) substitutions on the distal phosphate groups of the core structure and wherein the OMVs are not chemically detoxified and/or treated with formaldehyde, formalin, glutaraldehyde, hydrogen peroxide and combinations or derivatives thereof.

Embodiment 61. An immunogenic composition comprising (a) *Bordetella pertussis* Outer Membrane Vesicles (OMVs) comprising genetically detoxified pertussis toxoid, (b) an acellular pertussis antigen, (c) a tetanus toxoid and (d) a diphtheria toxoid.

Embodiment 62. An immunogenic composition comprising (a) *Bordetella pertussis* Outer Membrane Vesicles (OMVs) comprising genetically detoxified pertussis toxoid, wherein Lipid A in the OMVs has a modified structure lacking glucosamine (GlcN) substitutions on the distal phosphate groups of the core structure, (b) an acellular pertussis antigen, (c) a tetanus toxoid and (d) a diphtheria toxoid.

Embodiment 63. An immunogenic composition comprising (a) *Bordetella pertussis* Outer Membrane Vesicles (OMVs) comprising the genetically detoxified pertussis toxoid PT-9K/129G, (b) an acellular pertussis antigen, (c) a tetanus toxoid and (d) a diphtheria toxoid.

Embodiment 64. An immunogenic composition comprising (a) *Bordetella pertussis* Outer Membrane Vesicles (OMVs) comprising the genetically detoxified pertussis toxoid PT-9K/129G, wherein Lipid A in the OMVs has a modified structure lacking glucosamine (GlcN) substitutions on the distal phosphate groups of the core structure, (b) an acellular pertussis antigen, (c) a tetanus toxoid and (d) a diphtheria toxoid.

Embodiment 65. The immunogenic composition of Embodiment 61 to 64 wherein 100% of the pertussis toxoid in the Outer Membrane Vesicles is genetically detoxified PT.

Embodiment 66. The immunogenic composition of Embodiment 61 to 65 wherein 100% of the pertussis toxoid in the Outer Membrane Vesicles is the genetically detoxified pertussis toxoid PT 9K/129G.

General

The term “comprising” encompasses “including” e.g. a composition “comprising” X may include something additional e.g. X+Y. The word “substantially” does not exclude “completely” e.g. a composition which is “substantially free” from Y may be completely free from Y. In some implementations, the term “comprising” refers to the inclusion of the indicated active agent, such as recited polypeptides, as well as inclusion of other active agents, and pharmaceutically acceptable carriers, excipients, emollients, stabilizers, etc., as are known in the pharmaceutical industry. In some implementations, the term “consisting essentially of” refers to a composition, whose only active ingredient is the indicated active ingredient(s), for example antigens, however, other compounds may be included which are for stabilizing, preserving, etc. the formulation, but are not involved directly in the therapeutic effect of the indicated active ingredient. Use of the transitional phrase “consisting essentially” means that the scope of a claim is to be interpreted to encompass the specified materials or steps recited in the claim, and those that do not materially affect the basic and novel characteristic(s) of the claimed invention. See, In re Herz, 537 F.2d 549, 551-52, 190 USPQ 461, 463 (CCPA 1976) (emphasis in the original); see also MPEP § 2111.03. Thus, the term “consisting essentially of” when used in a claim of this invention is not intended to be interpreted to be equivalent to “comprising”. The term “consisting of” and variations thereof means limited to” unless expressly specified otherwise. In certain territories, the term “comprising an active ingredient consisting of” may be used in place of “consisting essentially”. The term “about” in relation to a numerical value x means, for example, x±10%, x±5%, x±4%, x±3%, x±2%, x±1%, The word “substantially” does not exclude “completely” e.g. a composition which is “substantially free” from Y may be completely free from Y. Where necessary, the word “substantially” may be omitted from the definition of the invention. Where methods refer to steps of administration, for example as (a), (b), (c), etc., these are intended to be sequential, i.e., step (c) follows step (b) which is preceded by step (a). Antibodies will generally be specific for their target, i.e., they will have a higher affinity for the target than for an irrelevant control protein, such as bovine serum albumin.

Unless specifically stated, a process comprising a step of mixing two or more components does not require any specific order of mixing. Thus components can be mixed in any order. Where there are three components then two components can be combined with each other, and then the combination may be combined with the third component, etc.

Antibodies will generally be specific for their target. Thus they will have a higher affinity for the target than for an irrelevant control protein, such as bovine serum albumin.

Where a component is described as being "adsorbed" to an adjuvant, it is preferred that at least 50% (by weight) of that antigen is adsorbed e.g. 50%, 60%, 70%, 80%, 90%, 95%, 98% or more. If a component is totally adsorbed then none should detectable in the supernatant of a composition after centrifugation.

Amounts of conjugates are generally given in terms of mass of saccharide (i.e. the dose of the conjugate (carrier+saccharide) as a whole is higher than the stated dose) in order to avoid variation due to choice of carrier.

Where animal (and particularly bovine) materials are used in the culture of cells, they should be obtained from sources that are free from transmissible spongiform encephalopathies (TSEs), and in particular free from bovine spongiform encephalopathy (BSE).

MODES FOR CARRYING OUT THE INVENTION

Materials and Methods

TdaP Vaccine

Commercially available TdaP vaccines were used. The TdaP vaccine is adjuvanted with aluminium hydroxide and contains Tetanus toxoid, Diphtheria toxoid and Acellular Pertussis antigens (PT, FHA and 69K, also referred to as pertactin or PRN).

Bacterial Strains and Growth Conditions

The following *B. pertussis* strains were used in this study: W28 PT 9K/129G (Pizza et al., 1989) which carries a genetically detoxified pertussis toxin and its arnT Knockout (KO) derivative lacking the arnT gene generated as described below. Bacteria were generally stored and grown as described in Gasperini et al., 2018 and briefly as follows: Bacteria were stored at 80° C. and recovered by plating on Bordet-Gengou (BG) agar plates, supplemented with 15% (v/v) sheep blood, for 3 days at 37° C. Bacteria were then inoculated at initial 600 nm optical density (OD600) of 0.05-0.1 in Stainer-Scholte medium supplemented with 0.4% (w/v) L-cysteine monohydrochloride, 0.1% (w/v) FeSO4, 0.2% (w/v) ascorbic acid, 0.04% (w/v)nicotinic acid, 1% (w/v) reduced glutathione. Cultures were grown in rotary shakers at 37° C. Recombinant DH5 *E. coli* strains were stored at 80° C., recovered by plating on LB agar plates supplemented with 20 g/ml chloramphenicol for 16 h at 37° C. For liquid cultures, bacteria were inoculated in LB medium supplemented with 20 g/ml chloramphenicol and were grown in rotary shakers at 37° C. for 16 h.

Construction of arnT KO

To construct a *B. pertussis* arnT mutant strain, similar to what has been described in Geurtsen et al., 2009, we amplified a part of the DNA upstream of arnT from *B. pertussis* strain W28 PT-9K/129G by using primers 5'-ATAGAATTCACGCGGTGCGGCGCCAGCGC-3' (SEQ ID NO:1) and 5'-ATAGGATCCGCCAGGACCTGGCCTGGCC-3' (SEQ ID NO: 2), containing an EcoRI and BamHI sites (underlined). Additionally, a DNA fragment downstream of arnT was obtained by PCR with primers 5'-ATAGGATCCGGACGAAGCCTTCAAGGGGC-3' (SEQ ID NO: 3) and 5'-ATAAAGCTTCGTCCAGGCGCGCCAGCGC-3' (SEQ ID NO: 4), containing an BamHI and HindIII sites (underlined). Both PCR products were cloned into pUC19 together with a kanamicin resistance cassette (KanR) containing BamHI sites at both ends. Resulting plasmids pUC19-arn$T_{up}$-KanR-arn$T_{down}$ was digested with EcoRI and HindIII restriction enzymes and the resulting EcoRI-HindIII fragment was ligated into EcoRI-HindIII restricted suicide vector pSORTP1. The final construct, designated pSORTP1-arn$T_{KO}$ was used to construct a *B. pertussis* (strain W28 PT9K/129G) arnT mutant by allelic exchange. Transformants were screened by PCR using various primer sets.

OMV Purification

OMVs were generated from W28 PT 9K/129G and its arnTKO derivative. Liquid cultures of *B. pertussis* were recovered after a 3-day growth in 250 mL baffled flasks. The liquid-air volume ratio resulted critical for OMV production yield and was kept at 1:5 ratio. Bacteria were then pelleted through centrifugation at 5,000×g for 30 minutes. Cell-free supernatants were recovered and filtered through 0.22 μm Stericups filters (Millipore). After ultracentrifugation at 175,000×g for 2 hours, the resulting OMV pellet was washed with Dulbecco's Phosphate-Buffered Saline (D-PBS), further ultracentrifuged at 175,000×g for 2 hours and finally resuspended in 100 μl D-PBS. OMV were quantified through the Lowry assay (DC Protein Assay, BioRad) for total protein content following the manufacturer's instructions.

Results

Outer membrane vesicle preparations were prepared from two *B. pertussis* detoxified vaccine strains, the W28 PT 9K/129G strain expressing a genetically detoxified pertussis toxin, and a derivative of the strain W28 PT 9K/129G arnTKO with a genetically modified lipidA structure lacking the glucosamine substitutions on the distal phosphate groups of the core structure, through deletion of the ArnT encoding gene. The arnT KO mutant of the W28 PT 9K/129G (Bp-Δarnt) exhibits 10-fold less TLR4 engagement FIG. 1(*a*) and induces significantly less IL-6 secretion from PBMCs than the W28 PT 9K/129G (Bp-WT) strain FIG. 1(*b*).

Figure 2:
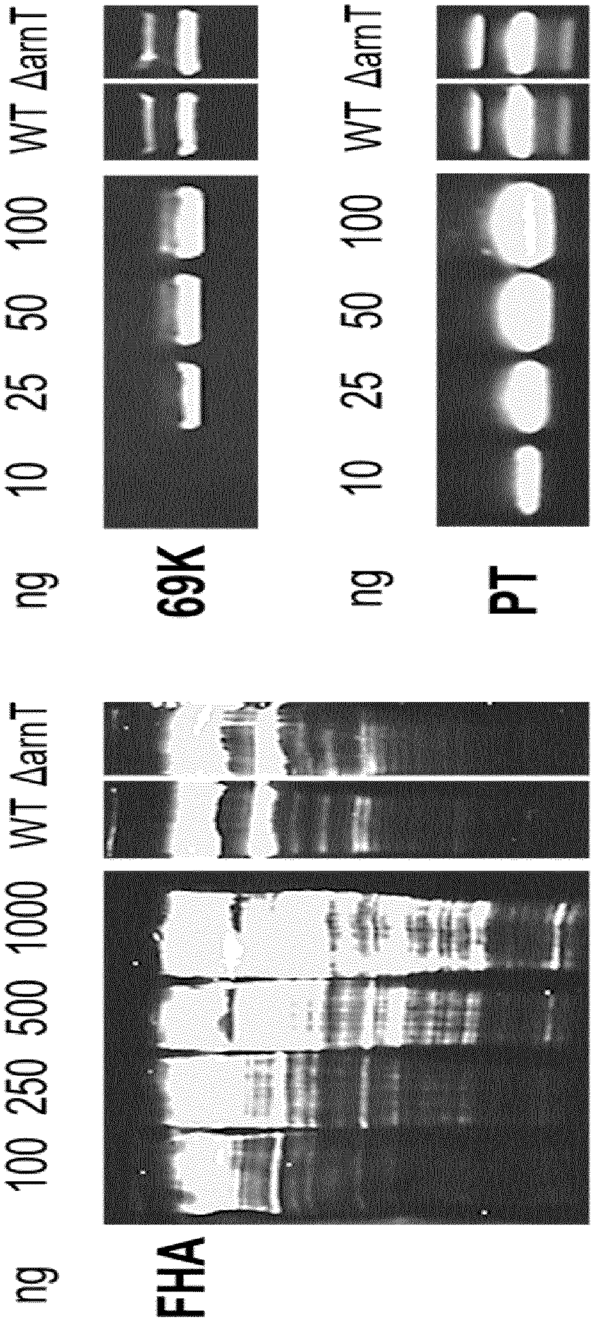
FIG. 2: OMV prepared from vaccine strains contain FHA, 69K and PT acellular pertussis antigens. Western Blots of titrated standard of purified FHA, 69K and PT acellular pertussis antigen subunits loaded at indicated quantities along with 1 ug of OMV from W28 PT 9K/129G (WT) and W28 PT 9K/129G arnTKO (Aarnt) strains, immunostained with anti-FHA; anti-69K and anti-PT antisera.
Figure 3A:
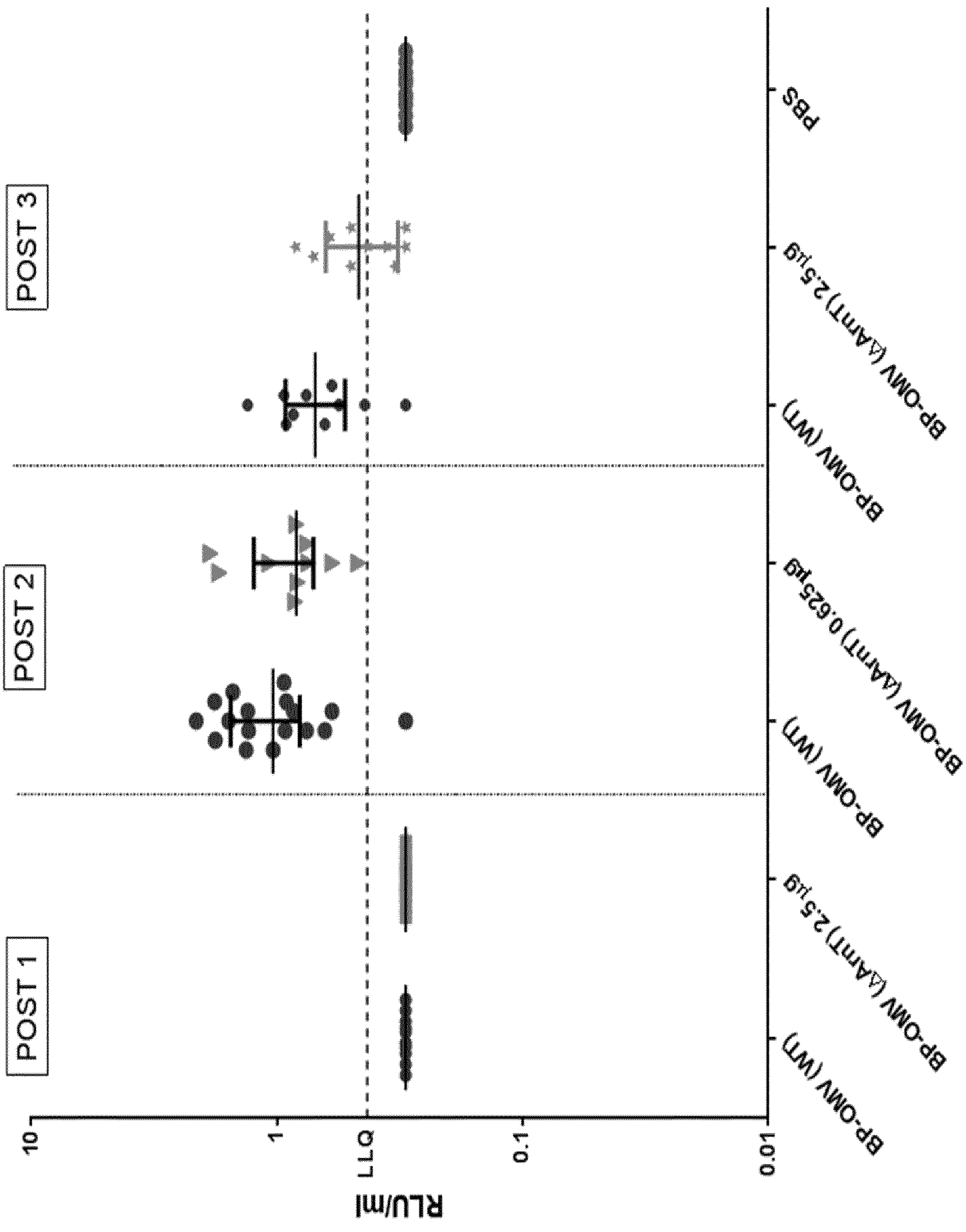
FIG. 3: Immunisation with OMV results in low levels of anti-aP antigen antibodies in mice. Mice were immunised intraperitoneally with 2.5 μg of OMV from the W28 PT 9K/129G (Bp-OMV (WT)) and W28 PT 9K/129G arnTKO (BP-OMV (ΔArnt)) 3 times 3 weeks apart. While only anti-69K antibodies could be detected after the 1st immunization, low levels of all 3 antigens (FHA, 69K, and PT) were detectable after the second and third dose by Luminex assay.
Figure 3B:
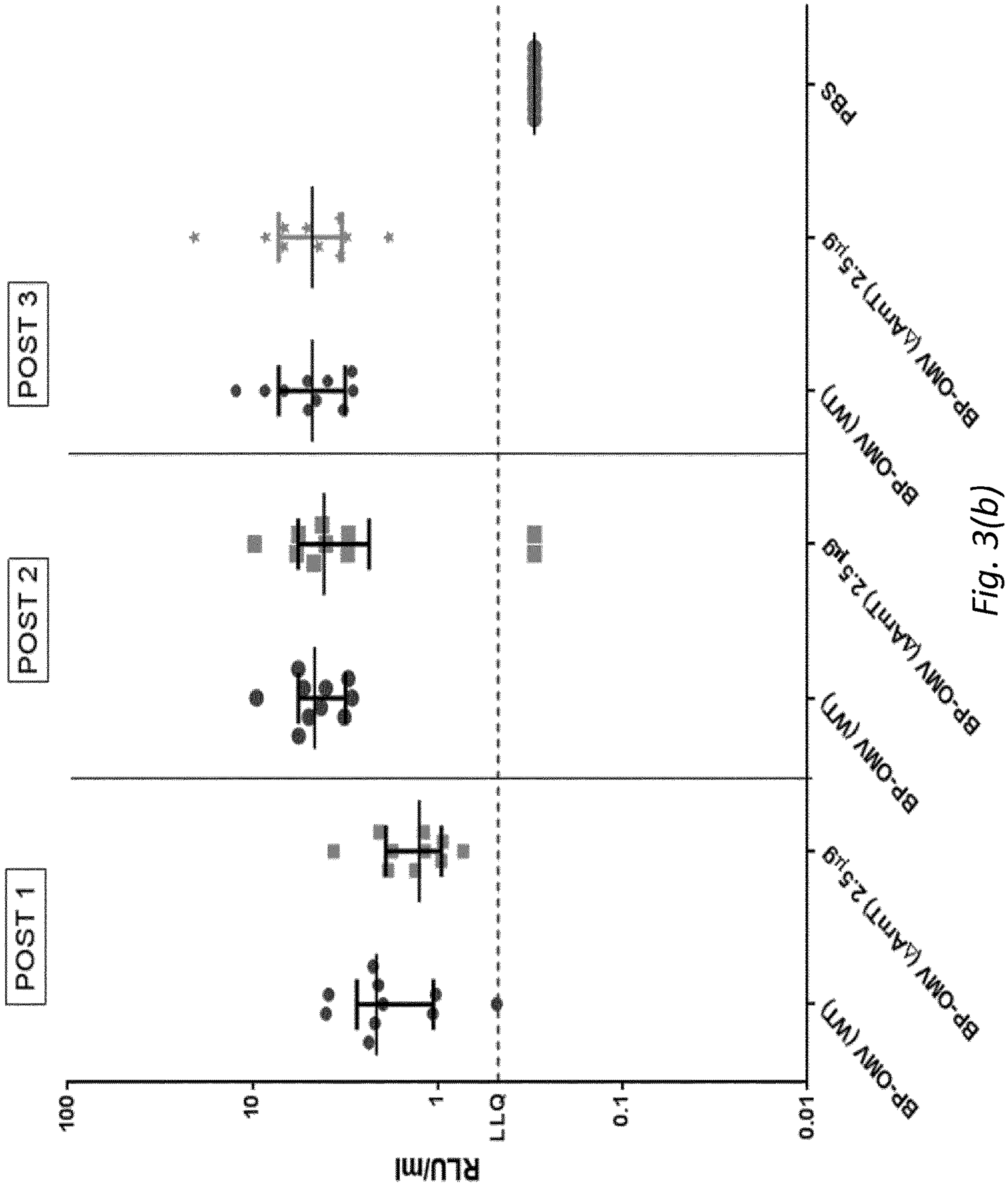
Figure 3C:
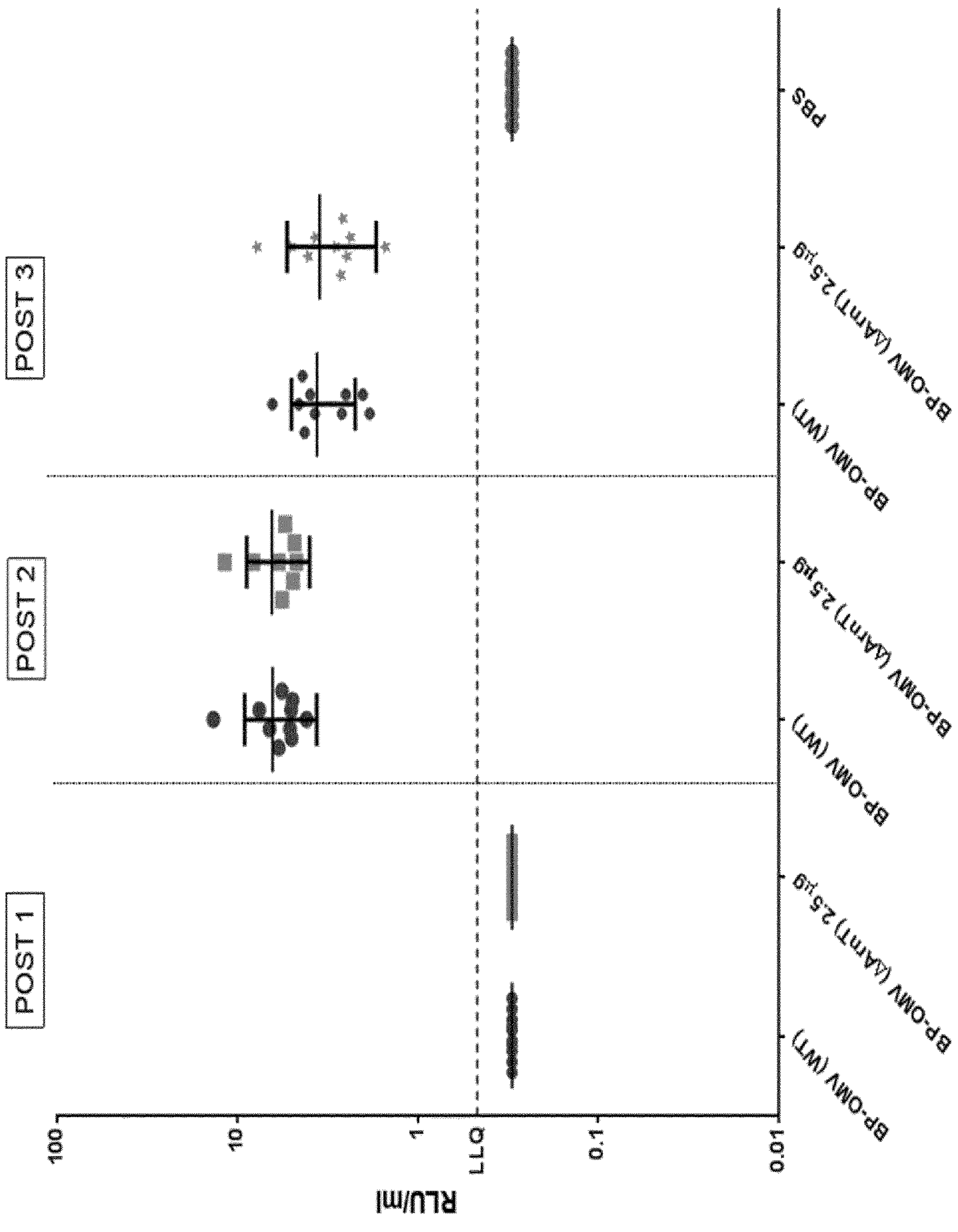

Both OMVS from the W28 9K/129G (Bp WT) and the W28 9K/129G arntKO (Bp ΔarnT) vaccine strains were shown to contain low amounts of the FHA, 69K and pertussis toxin components (FIG. 2). And mice immunised with both OMVs, elicited detectable levels of anti-bodies to all three acellular pertussis components (FIG. 3).

Mouse Immunisations for Generation of Mouse Antiserum

BALB/c mice (female, 6-weeks-old) (Charles River Laboratories International Inc., Wilmington, MA) received either three intraperitoneal (IP) immunisations three weeks apart or two intramuscular (IM) immunizations 4 weeks apart, with 100 μl formulations (50 μL/leg). Sera were collected 2 weeks after each immunization. OMV were formulated at doses indicated for each study in 2 mg/mL $Al(OH)_3$. For the combination formulations the OMV were formulated at doses of 0.1, 0.5 and 2.5 μg doses with ⅕ of human dose of TdaP antigens (see below) in a total volume of 100 μl in 2 mg/mL $Al(OH)_3$

| TdaP vaccine human dose (0.5 mL) | | | | | |
|---|---|---|---|---|---|
| PT | FHA | 69K | D | T | $Al(OH)_3$ |
| 4 μg | 4 μg | 8 μg | 2 Lf (1.2 μg) | 5 Lf (3.2 μg) | 1 mg |

Luminex Immunoassay on Mouse Antisera

Figure 4:
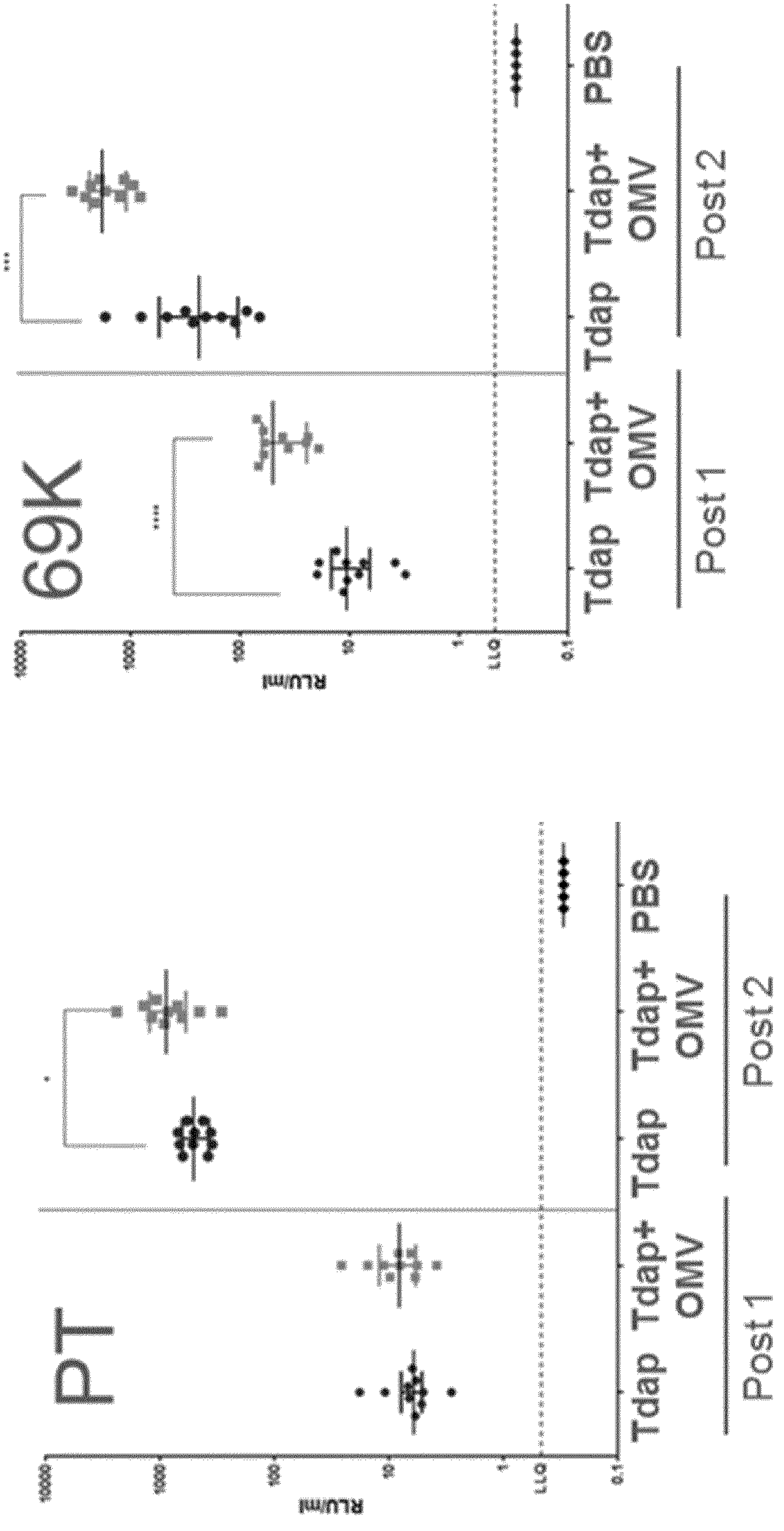
FIG. 4: Immunisation with TdaP in combination with OMV results in significantly higher levels of antibodies against most vaccine antigens as compared to TdaP alone Mice were immunized with Tdap (⅕ human dose) with or without the combination of 2.5 mg of OMV from the W28 PT 9K/129G arnTKO strain intramuscularly and following two immunizations sera were collected and analysed to measure the levels of antibody to each of the TdaP antigens by Luminex assay. *$p<0.001$,$p<0.01$ *$p<0.05$.
Figure 4:
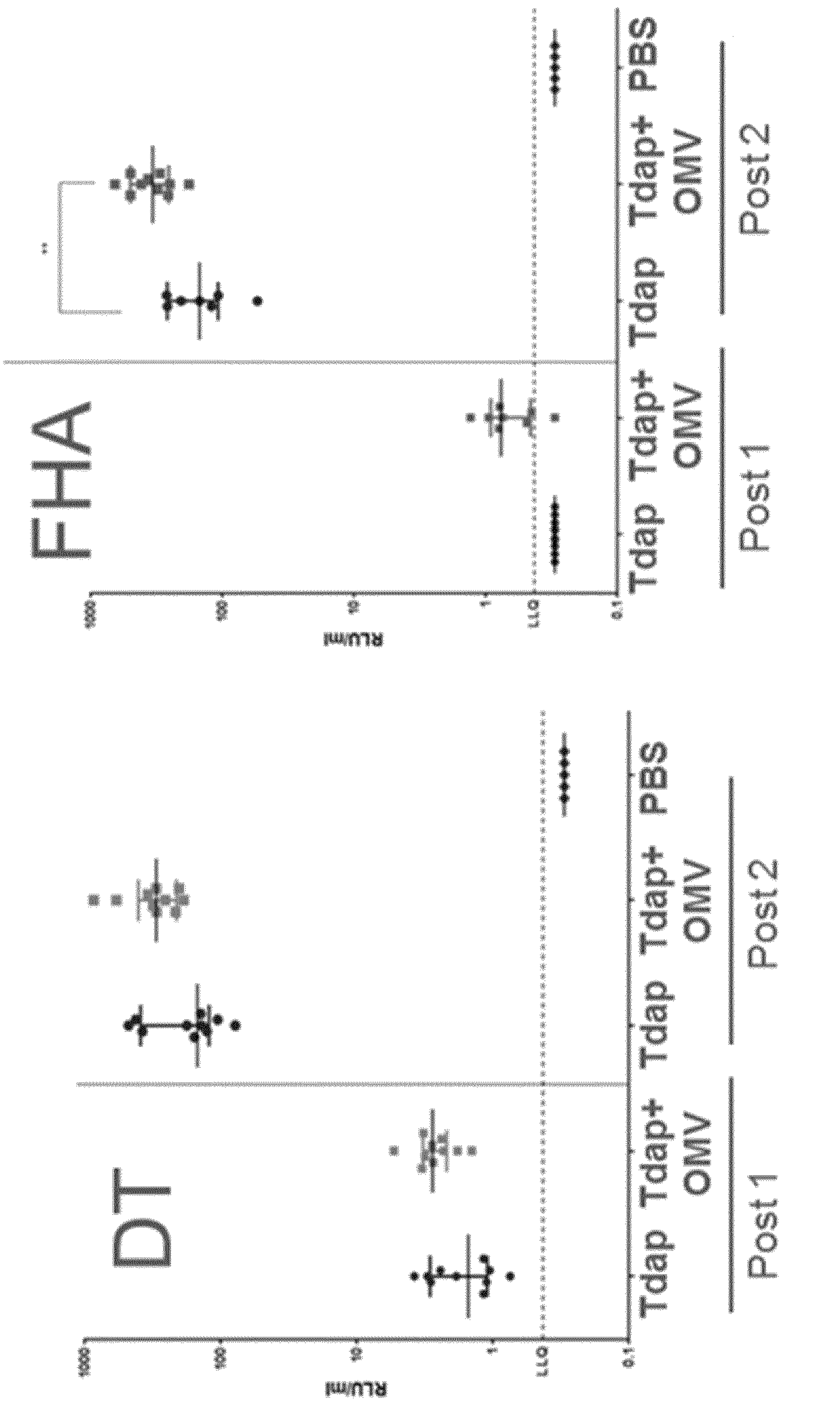
Figure 4:
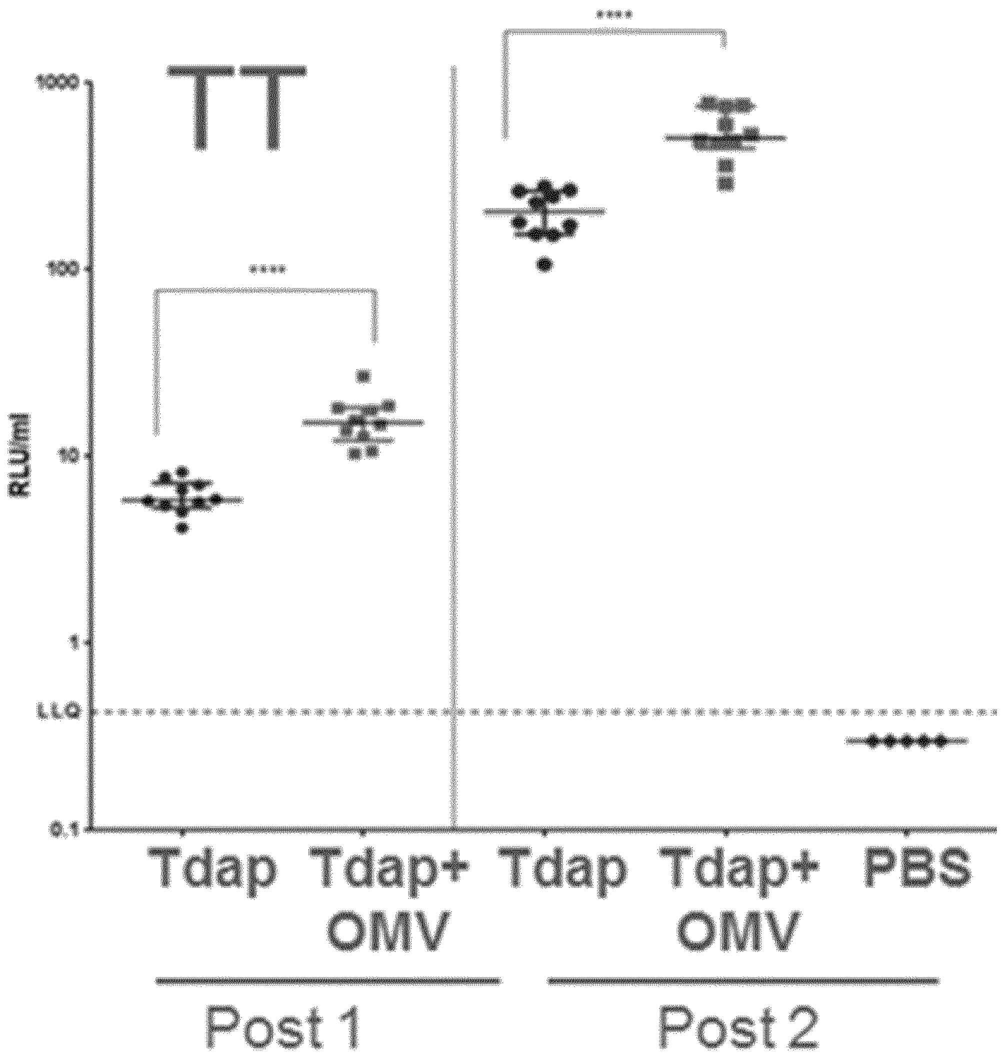

Total IgG titres against all vaccine antigens were analysed by Luminex penta-plex immunoassay as described (Agnolon et al., 2015) and as follows. Titres are expressed as Relative Luminex Units per ml (RLU/ml), resulting from conversion of the registered median fluorescence intensities (MFI) through hyper-immune reference antisera. A Luminex penta-plex immunoassay based on MagPlex microspheres was developed according to manufacturer's instructions to quantify anti-TdaP antibody titers in mouse sera. IgG titers were determined in individual animals after incubation of antigen-coupled microspheres with diluted sera (1:10000, post-1; 1:20000, post-2). Phycoerythrin-conjugated secondary antibody was used for detection (1:400). IgG measurements were determined as median fluorescence intensities (MFI) on the Luminex FLEXMAP 3D analyzer (Luminex Corporation, Austin, TX) using the Bio-Plex Manager 5.0 software (Bio-Rad, Hercules, CA). An antiserum specific for each antigen was used as reference to convert MFI values of total IgG in RLU/ml (Relative Luminex Units). The limit of quantification (LOQ) of the assay was determined for each antigen and was considered as threshold for positive results. Results are shown in FIG. 4.

Adhesion Inhibition Assay

For *B. pertussis* adhesion inhibition assay, bacteria were grown for 16 h in liquid culture and then pelleted at 8000×g for 5 min and resuspended in d-PBS at $OD_{600}$ 0.5. For the fluorescent labeling of *B. pertussis* cells, a volume of 445 μl of bacterial suspension was then mixed with 50 μl of 1 m $NaHCO_3$ and 5 μl of Alexa Fluor 488 Carboxylic Acid, Succinimidyl Ester (Life Technologies, Waltham, MA) and incubated for 15 min at 37° C. After centrifugation at 8,000×g for 5 min at room temperature, supernatant was removed and pellet was washed once with 1 ml d-PBS to remove unbound dye and bacteria were finally resuspended in F12-K medium at $OD_{600}$ 0.2. Pooled mouse sera were 4-fold serially diluted in F-12K medium containing 1% (v/v) naïve mouse serum and incubated with labeled *B. pertussis* for 1 h at 37° C. in 1:1 ratio. One hundred microliters of bacteria/serum mixtures were transferred in triplicate onto plated A549 cells. Infected cells were incubated for 1 h at 37° C. After extensive washing to remove unbound bacteria, fluorescence was measured at excitation/emission 485/535 nm by Tecan Infinite F200PRO microplate reader.

Figure 5:
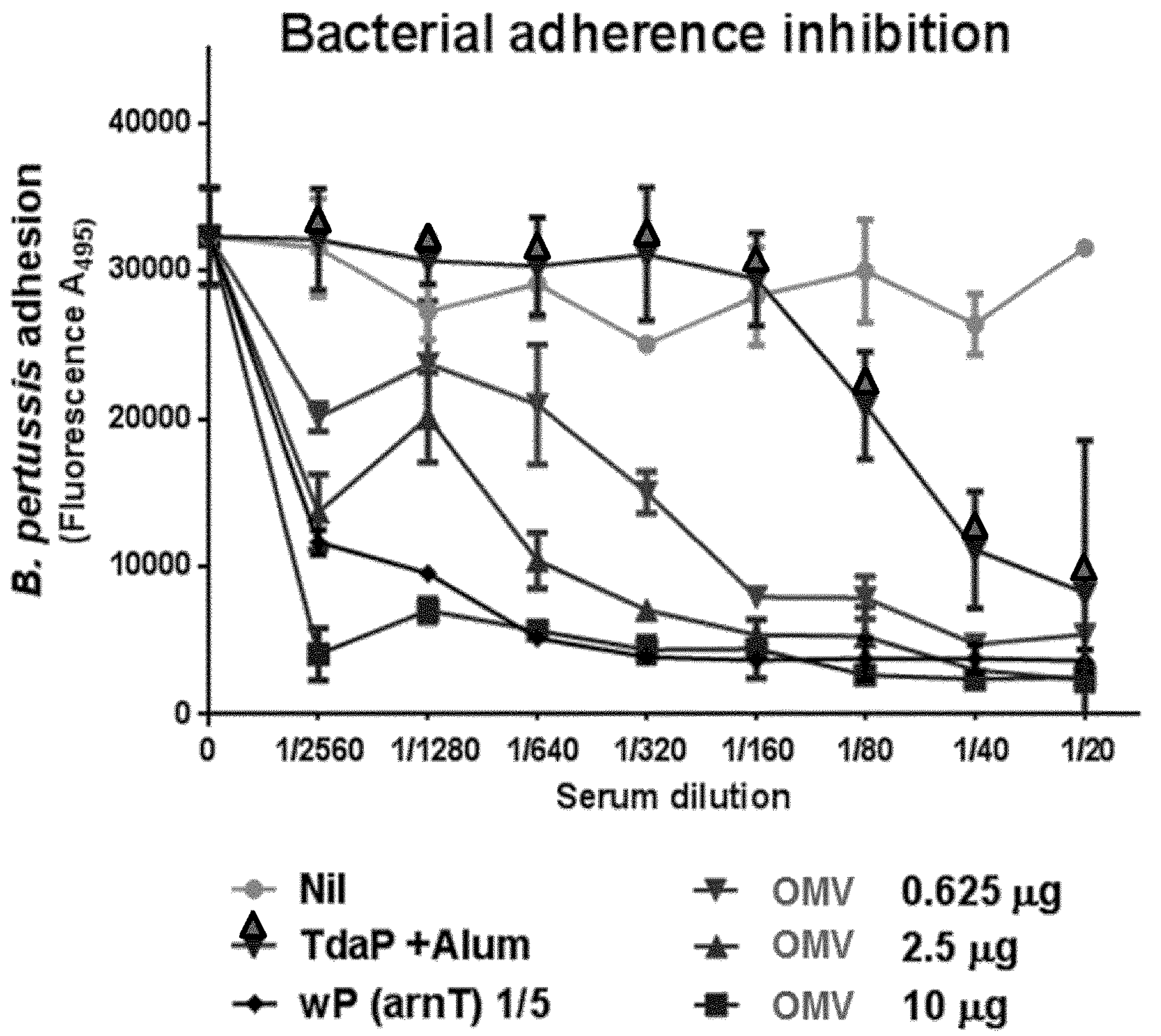
FIG. 5: OMV elicit antibodies that inhibit A pertussis adhesion to epithelial cells in vitro similarly to the wP vaccine. Sera from 10 mice per group immunized with either OMV (from W28 9K/129G arntKO), whole bacteria (from the W28 9K/129G arntKO), TdaP vaccine or aluminum hydroxide as control (nil) were pooled, serially diluted in infection medium and incubated with labeled wild-type *B. pertussis* BP536 for 1 h. A549 cells were then infected with the bacteria/sera mixtures for 1 h and, after extensive washes to remove unbound bacteria, cell-associated bacteria were quantified by fluorescence reading at Ex/Em 485/535 nm. Results represent mean+/−S.D. of one representative of three independent experiments each performed in triplicates.

Immunisation of mice with wP or the three different OMV doses resulted in the induction of antibodies that can inhibit the ability of *B. pertussis* to adhere to in vitro cell cultures of epithelial A549 cells. Sera from mice immunised with inactivated whole bacteria had the highest level bacterial adherence inhibition, and the bacterial adherence inhibition induced by the OMV vaccines was proportional to the antigen dose. The TdaP vaccine did not induce high levels of antibodies in mice that inhibit adhesion of fluorescently labelled bacteria and only low serum dilutions (1/40 and above) resulted in reduced fluorescence in the assay. OMV at the highest dose of 10 μg was found to induce antibodies upon vaccination that confer the highest level of bacterial adherence inhibition which was comparable to that induced by the whole bacteria control (FIG. 5).

Kendrick's Intracranial Challenge Potency Test

CD1 mice (6 weeks old) were vaccinated once intraperitoneally (i.p.) with 500 μL vaccine formulations and challenged 2 weeks post-immunisation with a 30 μl suspension of *B. pertussis* strain 18323 administered intracranially and the survival of the mice is followed for 2 weeks post-challenge according to the Kendrick intracranial challenge potency test (Kendrick et al., 1947) and in accordance with the European Pharmacopoeia guidelines. The NIBSC standard at three doses (1/10, 1/50 and 1/250 human dose) was used as positive control, and the OMV were formulated at 0.4, 2 and 10 μg doses in 2 mg/mL $Al(OH)_3$.

Figure 6:
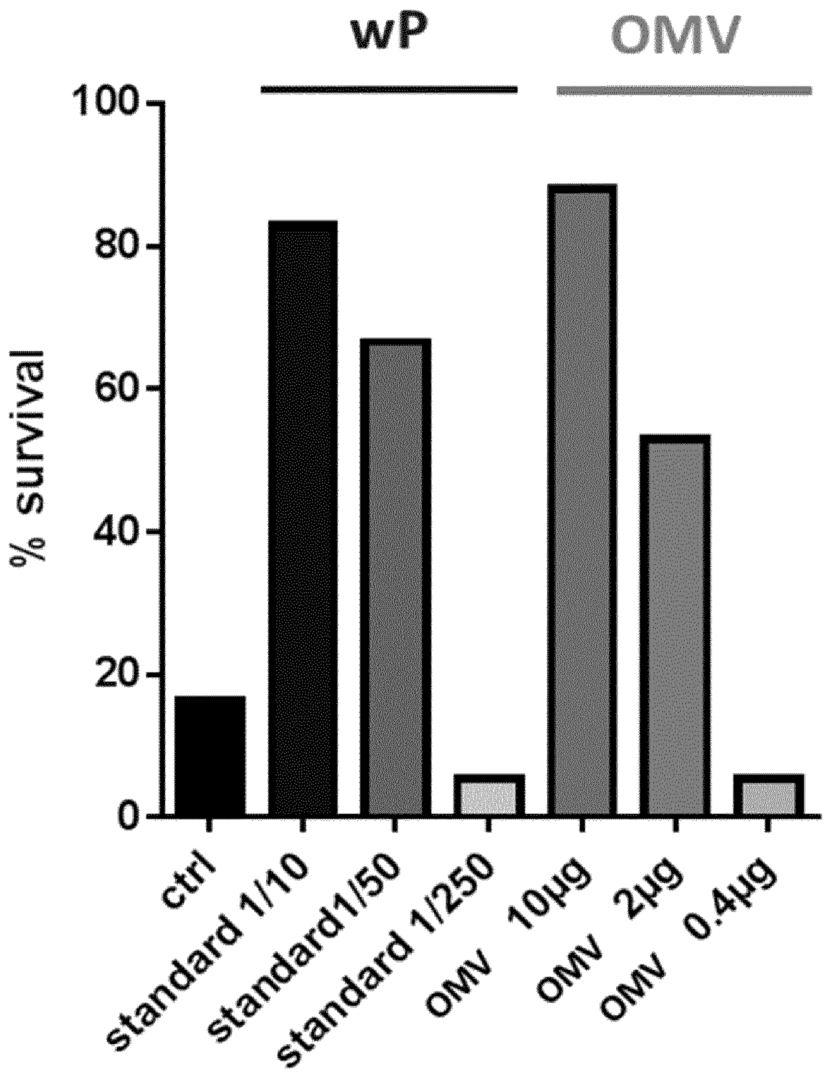
FIG. 6: OMV elicit a potent protective response similar to the wP vaccine standard against intracranial challenge of *B. perussis* in the Kendrick Test. Mice were immunised once intraperitoneally with whole cell vaccine or OMV formulations and challenged 2 weeks post-immunisation with a suspension of *B. pertussis* strain 18323 administered intracranially. The survival of the mice is reported 2 weeks post-challenge according to the Kendrick intracranial challenge potency test. Vaccines formulations include the wP whole cell pertussis vaccine (standard) at 1/10, 1/50 and 1/250 of the human dose and OMV from the W28 9K/129G strain (OMV) at indicated doses.
Figure 7A:
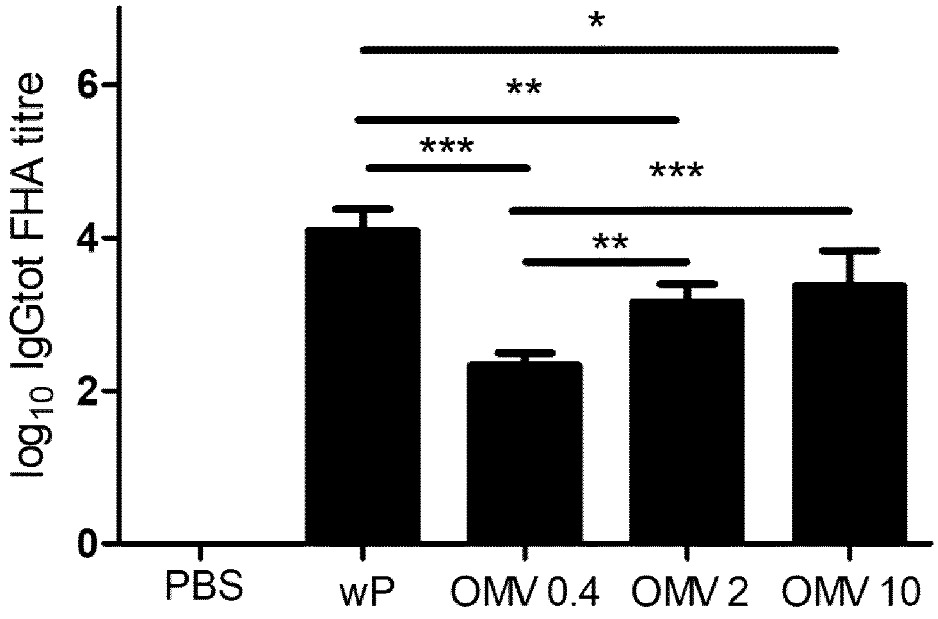
FIG. 7: FHA-specific total IgG (FIG. 7(*a*)) and IgG2c (FIG. 7(*b*)) serum titres are proportional to OMV vaccine dose. FHA-specific antibodies present in the sera of immunised mice on the day of challenge were analysed by ELISA. *$p<0.001$, $p<0.01$, *$p<0.05$, n.s.=not significant.
Figure 7B:
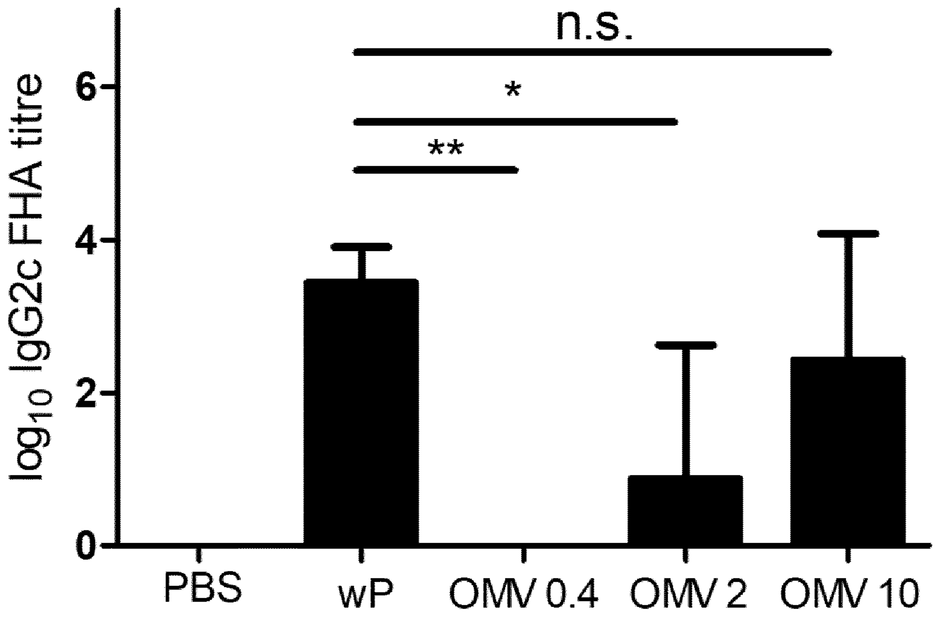
Figure 7C:
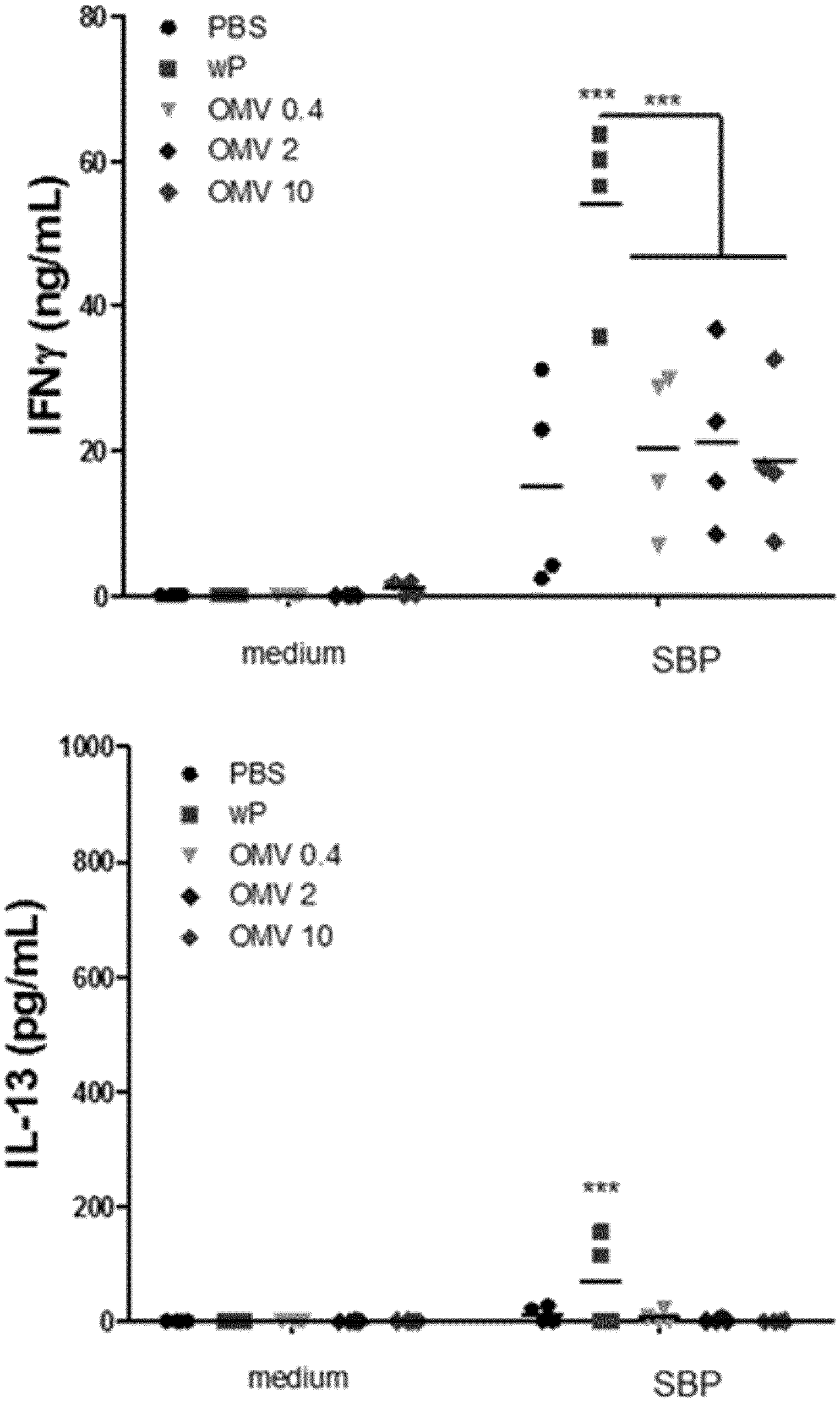
Figure 7C:
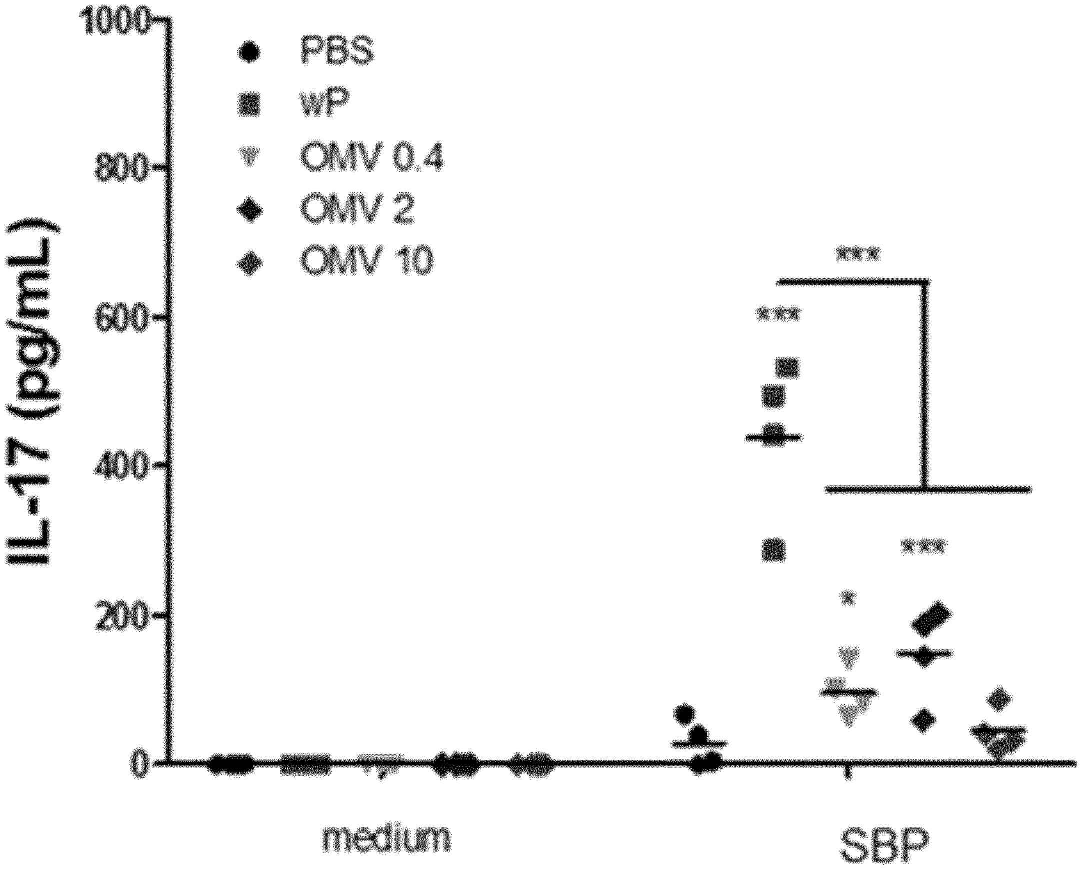

The intracerebral mouse protection test (Kendrick test) is effective for determining the potency of whole-cell pertussis vaccines and is the only test that has shown a correlation with protection in children (Xing et al., 201440). Immunisation of mice with OMV at increasing doses (at 0.4, 2 and 10 μg doses) conferred increasing levels of protection against intracranial challenge with *B. pertussis* (FIG. 6) that was comparable to the wP NIBSC standard. The protection induced by the OMV vaccines was proportional to the antigen dose and successful in eliciting a potent protective response that was comparable to that of the wP (FIG. 6).

Aerosol Challenge

C57BL/J6 mice (female, 10-weeks-old) were vaccinated once intraperitoneally (i.p.) with 100 μl vaccine formulations and challenged 3 weeks later as described previous (Misiak et al., 2017a) and below. The whole cell pertussis (wP) vaccine was used as a positive control at 1/5 or 1/10 of the human dose as indicated. OMV were formulated at 0.4, 2, and 10 μg doses as indicated in 2 mg/mL $Al(OH)_3$. For the combination formulations the OMV were formulated at 2.5 μg dose with 1/5 of human dose of TdaP antigens (see below) in a total volume of 100 μl in 2 mg/mL $Al(OH)_3$

| TdaP human dose (0.5 mL dose volume) | PT (8 μg) | FHA (8 μg) | PRN (2.5 μg) | TT (5 Lf) | DT (2 Lf) | Alum (1 mg) |
|---|---|---|---|---|---|---|

Serum and spleens were collected from immunised mice (4 mice per group) at 3 weeks post vaccination, one day prior to the challenge. Antigen-specific cytokine production by spleen cells and serum antibodies were analysed by ELISA. The remaining mice were then challenged with virulent strain of *B. pertussis* as described below and lung CFUs were assessed at 1, 3, 7 and 14 days post infection.

Respiratory infection of mice was performed by exposing mice to *B. pertussis* aerosol (BP338 strain; $1\times10^9$ CFU/ml) for 10 min followed by 10 min rest using PARI TurboBOY SX nebulizer. The course of *B. pertussis* infection was followed by performing CFU counts on lungs from groups of three to four mice at intervals after challenge. The lungs were aseptically removed and homogenized in 1 ml of sterile physiological saline with 1% casein. Undiluted and serially diluted homogenate (100 μl) from individual lungs was plated in duplicate on Bordet-Gengou agar plates and the bacterial colonies were counted after 6 d incubation at 37° C.

Antibody titres were measured by ELISA as described previously (Misiak et al., 2017b) and as follows. FHA-specific antibodies were quantified by ELISA using plate-bound FHA (1 μg/mL), biotin-conjugated anti-mouse IgG1 or IgG2a and peroxidase-conjugated streptavidin (BD Pharmingen, Franklin Lakes, NJ). Antibody levels are expressed as the mean end point titre f SEM, determined by extrapolation of the linear part of the titration curve to 2 SE above the background value obtained with nonimmune serum.

Immunisation of mice with wP and the three different OMV doses resulted in the induction of *B. pertussis* specific antibody production. wP promoted the highest anti-FHA total IgG titres, which were significantly greater compared with all three OMV doses (FIG. 7). Vaccination with wP was found to promote the highest TH1 responses and accordingly the highest anti-FHA IgG2c titre (FIG. 7). Anti-FHA IgG2c was detected in sera of 1 out of 4 and 3 out of 4 OMV 2 and OMV 10 vaccinated mice, respectively. No FHA-specific IgG2c was detected in mice immunised with OMV 0.4. The differences in FHA-specific responses suggest a much lower FHA content in OMV when compared with wP.

Figure 8:
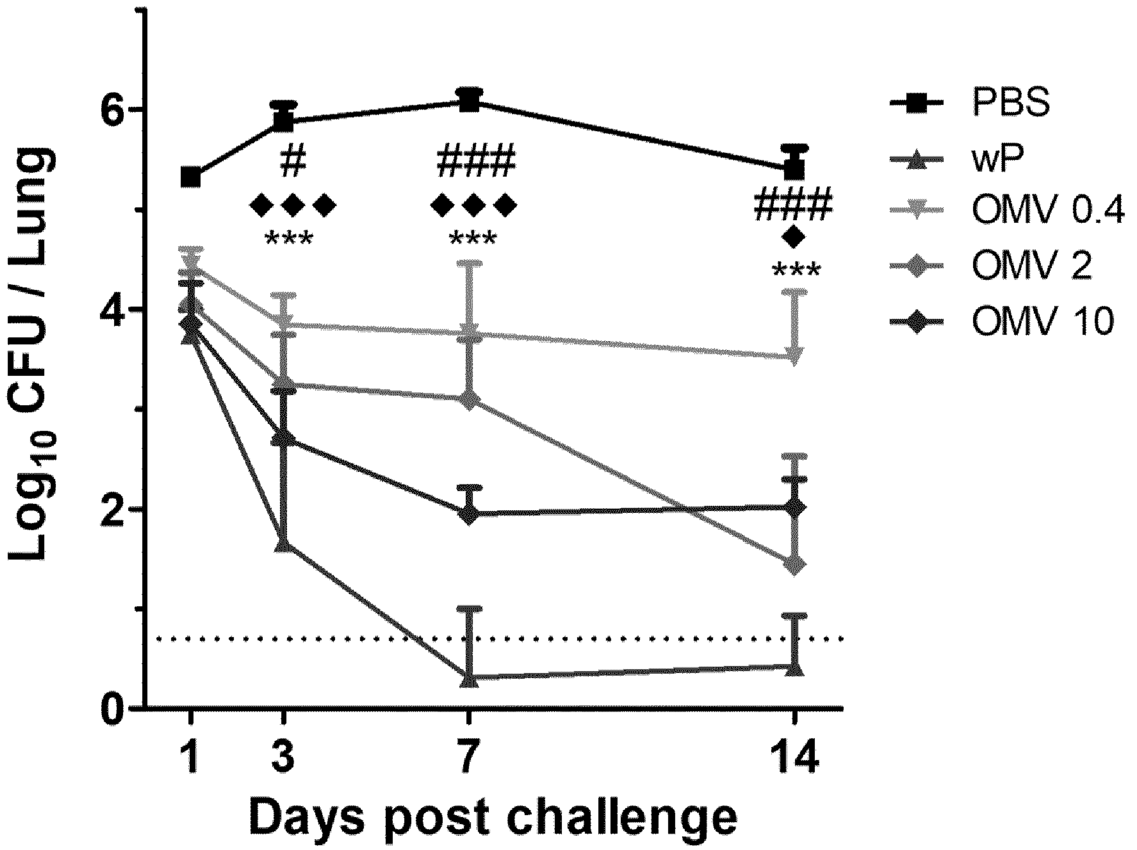
FIG. 8: Rate of A pertussis clearance from the lungs is directly proportional to the OMV vaccine dose. C57BL6 mice were immunised with PBS, wP, OMV 0.4, OMV 2, or with OMV 10 at 3 weeks prior to challenge. The mice were then infected with a virulent strain of *B. pertussis* (Bp338) and the bacterial burden in the lungs assessed by performing CFU counts on serially diluted lung homogenates at the time points indicated. Dashed line indicates the detection limit. ***$p<0.001$ wP vs OMV 0.4, ###$p<0.001$, #$p<0.05$ wP vs OMV 10, ♦♦♦$p<0.001$, ♦$p<0.05$ wP vs OMV 2.

High protective antibody titers together with induction of a TH1 response are key for protection against *B. pertussis*. Single dose immunisation with wP, OMV 0.4, OMV 2 and OMV 10 conferred different levels of protection against respiratory challenge with *B. pertussis* (FIG. 8). Mice immunised with wP vaccine had the highest level of protection and majority of them cleared the infection by day 7 post challenge. In addition, wP immunised mice had significantly lower CFU counts on all time points post infection compared with mice that received OMV vaccine at all three concentrations tested. The protection induced by the OMV vaccines was proportional to the antigen dose. However, OMV 10-induced protection was not as effective as that induced by wP vaccination. The areas under the clearance curves confirmed that wP was the best at protecting mice against *B. pertussis* aerosol challenge. OMV at the highest dose of 10 μg was found to confer the highest level of protection in mouse model of *B. pertussis* challenge. However, it was found to be still significantly less effective than the wP vaccine. FHA-specific IgG2c responses were also found to be the highest in mice that received the wP vaccine. and FHA-specific serum IgG2c which did increase with the OMV vaccine dose The data presented here shows that level of protection conferred by the OMV vaccines is directly proportional to the antigen dose used. It also highlights that, even at the highest dose chosen, OMV vaccines are not as protective as the wP.

Figure 9:
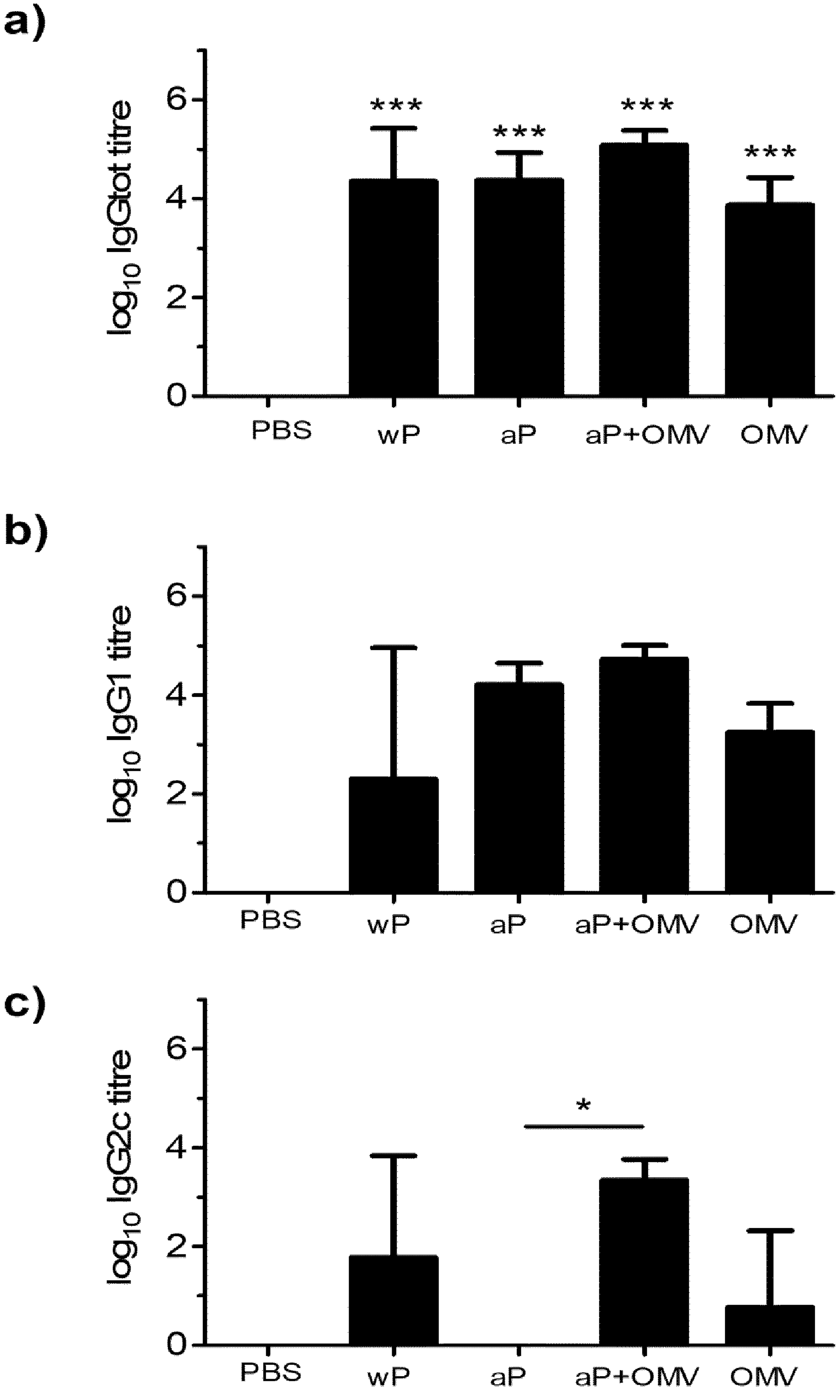
FIG. 9: aP formulated with OMV promotes FHA-specific serum IgG2c. FHA-specific antibodies present in the sera of immunised mice on the day of challenge were analysed by ELISA. ***$p<0.001$, *$p<0.05$.

To compare the protective efficacy against *B. pertussis* challenge that OMV may have when added in combination to the acellular pertussis formulation the aerosol challenge model was used with an acellular pertussis vaccine formulated with alum or with alum+OMV, with whole cell vaccine as a positive control. Immunisation of mice with wP, aP and aP+OMV induced high total anti-FHA IgG titres (FIG. 9). Furthermore, high total IgG titres were detected in the OMV only group. No significant differences were observed between the four vaccine groups. High anti-FHA IgG1 titres were detected in all vaccine groups with the highest IgG1 titres detected in the sera of aP and aP+OMV vaccinated mice (FIG. 9). However, no significant differences were detected between the groups. FHA-specific IgG2c was detected in the sera of 2 out of 4 wP, 4 out of 4 aP+OMV and 1 out of 4 OMV vaccinated mice (FIG. 9*c*). No anti-FHA IgG2c was detected in the aP group. The IgG2c response to aP alone was significantly augmented by addition of OMV.

Figure 10:
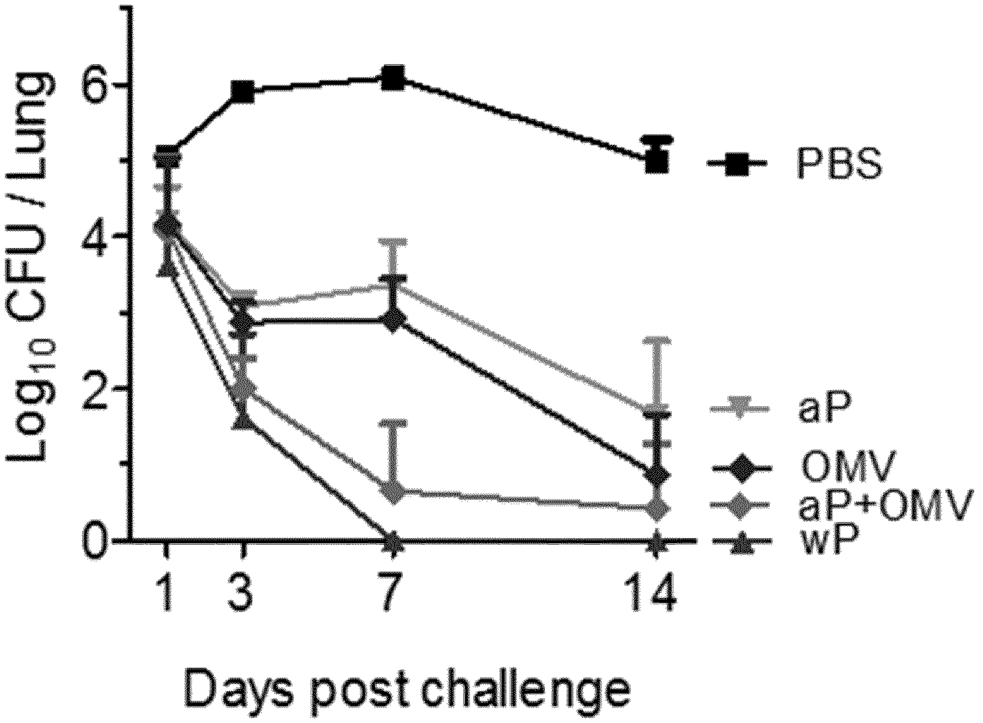
FIG. 10: Immunisation with wP, aP, aP+OMV and OMV alone confers protection against *B. pertussis* challenge. C57BL6 mice were immunised with PBS, wP, aP, aP+OMV or with OMV alone at 3 weeks prior to challenge. The mice were then infected with a virulent strain of *B. pertussis* (Bp338) and the bacterial burden in the lungs assessed by performing CFU counts on serially diluted lung homogenates at the time points indicated. *$p<0.001$, $p<0.01$, *$p<0.05$.
Figure 10:
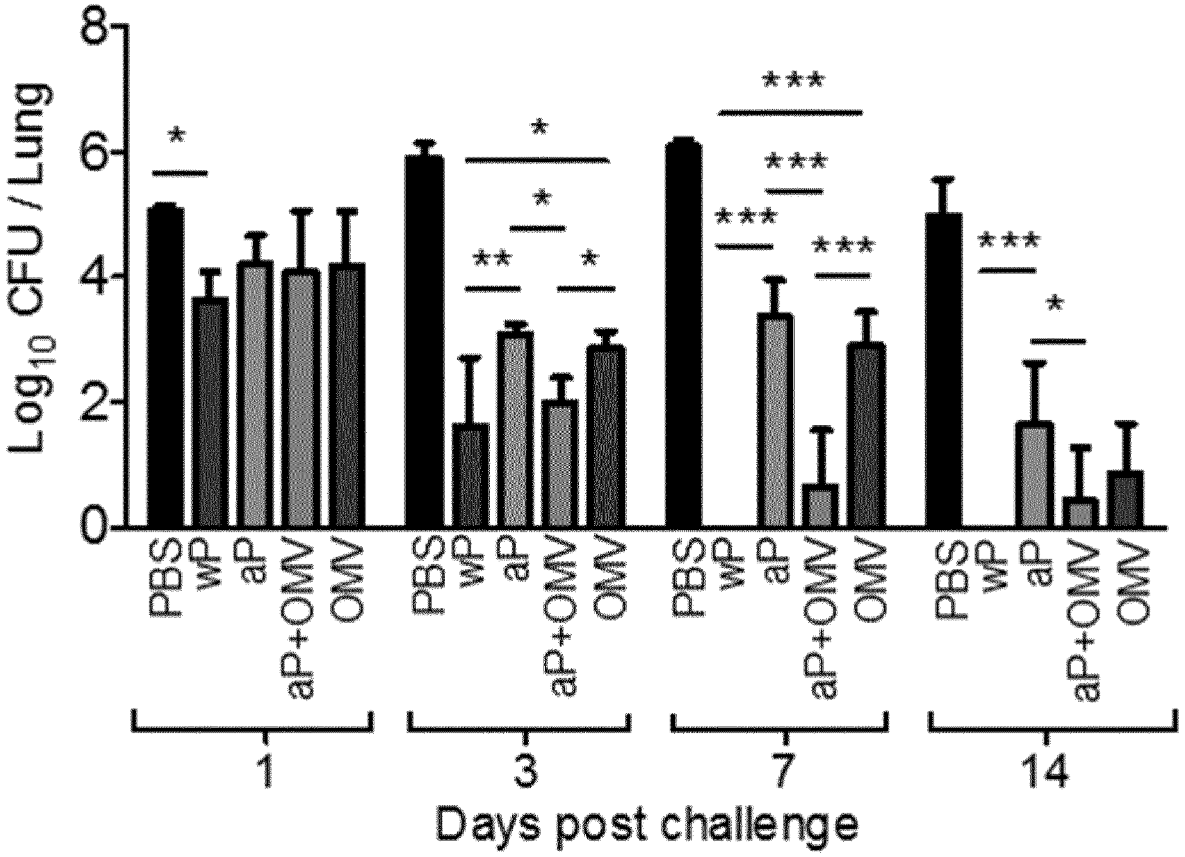

Single dose immunisation of mice with wP, aP, aP+OMV as well as with OMV alone was found to confer protection against respiratory challenge with *B. pertussis* (FIG. 10). Mice immunised with wP vaccine had the highest level of protection and cleared the infection by day 7 post challenge. aP and OMV vaccination conferred similar level of protection. However, these vaccines were significantly less effective than the wP vaccine. In contrast, the aP+OMV combination was found to confer a level of protection comparable to that induced by the wP vaccine. No significant differences were detected between these two vaccines on any of the time points tested. Areas under the clearance curves confirmed that wP and aP+OMV were the most potent of the tested vaccines.

Thus, a single immunisation with ⅕ human dose of all of the vaccine formulations tested induced protective immunity against *B. pertussis* in C57BL6 mice. Immunisation with OMV alone was also found to confer significant protection, which was comparable to that induced by the aP vaccine.

Figure 11:
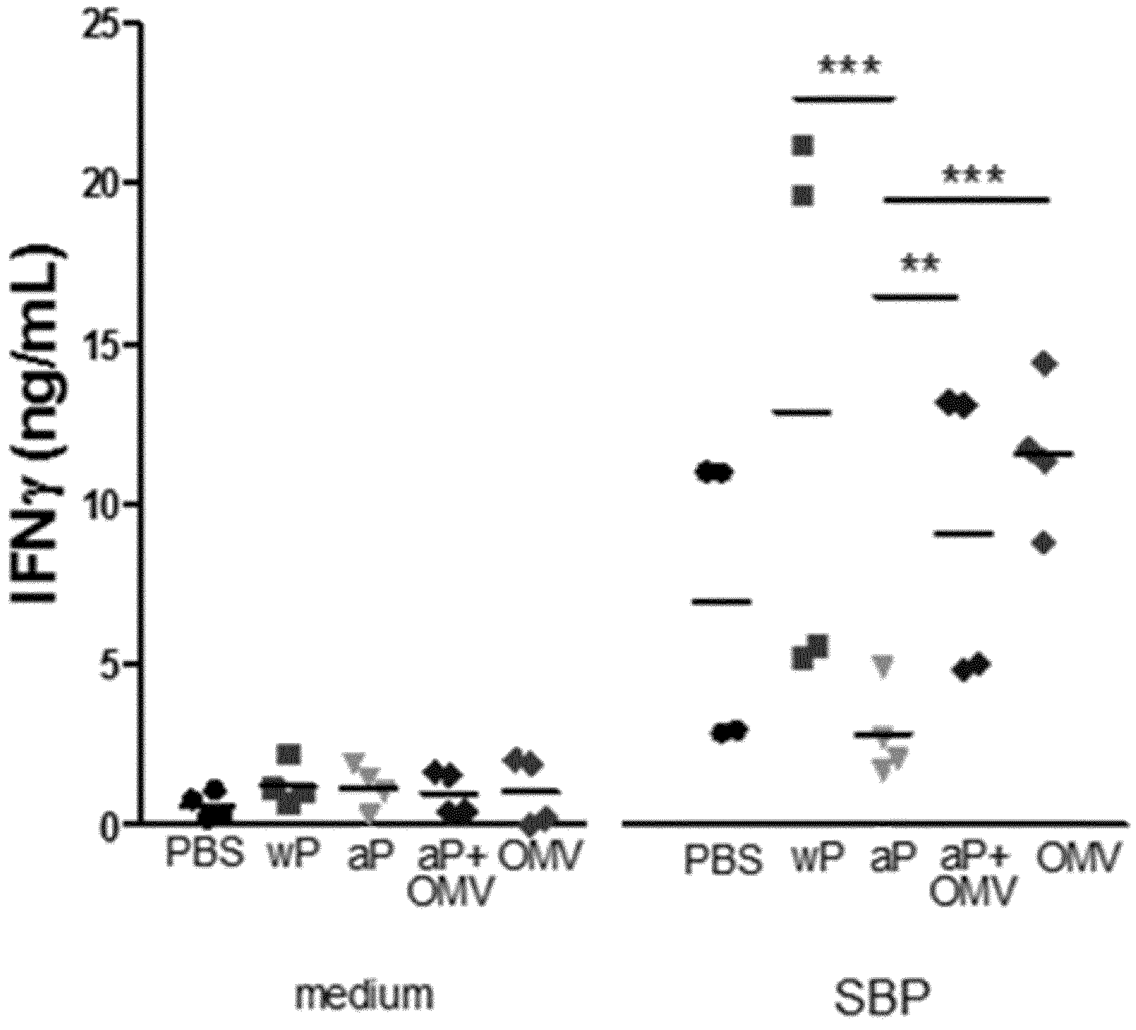
FIG. 11: Addition of OMV to an aP vaccine drives a favourable TH1 response. Spleen cells ($2\times10^6$/mL) from vaccinated C57BL6 mice were cultured in the presence of sonicated *B. pertussis* (SBP, 5 μg/mL). After 72 hours the concentration of IFNγ in the supernatants was analysed by ELISA.$p<0.01$, *$p<0.001$.

Strong Th1 responses were detectable in wP, aP+OMV and OMV alone, but not in aP vaccinated mice. Enhanced Th1 responses in the aP+OMV vaccinated mice compared to the mice that received the aP vaccine correlated with high anti-FHA IgG2c titres, which were virtually absent in the aP-immunised mice. The data presented here shows that addition of OMV to the aP vaccine strongly enhances its protective efficacy and induces a switch to anti-FHA IgG2c production and TH1 responses both during primary and booster vaccinations (FIG. 11).

Booster Vaccination

In previous experiments naïve mice were used for immunization. This would be the case for a primary vaccination (i.e. pediatric vaccines). Yet, booster vaccination is also required later in life and most subjects in developed countries will have received current commercially available vaccines that induce a more TH2-prone response. This situation was mimicked using a commercially available pediatric vaccine (Infanrix Hexa) for the first (primary) immunization and different commercially available or experimental booster formulations—including TdaP+OMV—for the secondary immunization.

Figure 12:
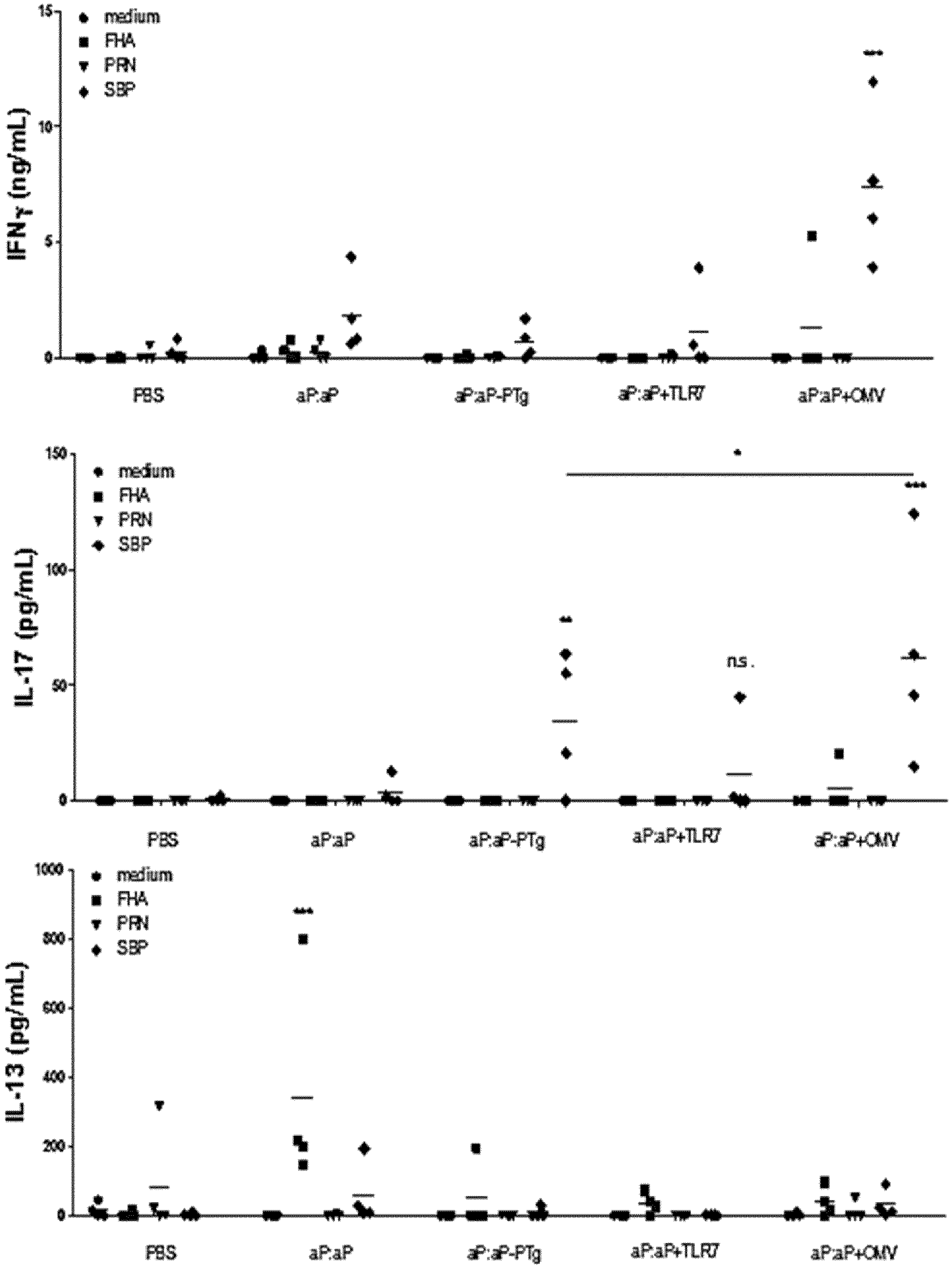
FIG. 12 aP+OMV booster promotes antigen specific IFNγ production in aP primed mice. Spleen cells ($2\times10^6$/mL) from vaccinated C57BL6 mice were cultured in the presence of FHA (2 μg/mL), PRN (2 μg/mL), sonicated *B. pertussis* (SBP, 5 μg/mL) or medium alone. After 72 hours the concentration of IFNγ, IL-17 and IL-13 in the supernatants was analysed by ELISA. *$p<0.05$, $p<0.01$, *$p<0.001$.

Addition of OMV to a TdaP vaccine enhanced TH1 responses significantly, while different TdaP vaccines even in the presence of an TH1-inducing adjuvant (Alum-TLR7) did not change the TH-balance (FIG. 12).

CONCLUSIONS

The following observations were made regarding the immunogenicity of the investigated vaccine formulations:

- OMVs, Diphtheria, Tetanus and Pertussis vaccines elicited specific antibody titers to the corresponding antigens, in mice immunized with all of the investigated formulations.
- No immunological interference was observed between OMVs and Tetanus/Diptheria/Pertussis vaccine combinations.
- IgG and functional antibody responses to vaccination with a combination of OMV/Diphtheria/Tetanus/Pertussis antigens yielded significantly higher titers than those observed following vaccination with OMV or TdaP vaccine alone.
- Addition of OMV to the aP vaccine induces a switch to anti-FHA IgG2c production and Th1 responses were detectable in wP, aP+OMV and OMV alone, but not in aP vaccinated mice.

Addition of OMV to the aP vaccine in a combination vaccine strongly enhances its protective efficacy with respect to the OMV or aP protective responses when administered alone. In conclusion, there was no evidence of strong interference between any of the investigated vaccines. Immunisation with OMV alone was found to confer significant protection in the Kendricks potency test and the aerosol challenge model. Addition of OMVs to acellular pertussis vaccines leads to greater protection than either aP or OMV vaccines alone. Without wishing to be bound by theory, this may be due to the additional protective antigens contained in the vesicles and/or to the induction of a favourable TH1 profile both at primary or booster vaccination.

It will be understood that the invention has been described by way of example only and modifications may be made whilst remaining within the scope and spirit of the invention.

REFERENCES

[1] Vaccines. (eds. Plotkin & Orenstein). 4th edition, 2004, ISBN: 0-7216-9688-0.
[2] Katial et al. 2002, Infect Immun, 70: 702-707
[3] WO2004/019977.
[4] European patent 0011243.
[5] Fredriksen et al. (1991) *NIPH Ann.* 14(2):67-80.
[6] WO01/91788.
[7] WO2005/004908.
[8] *Vaccines*. (eds. Plotkin & Orenstein). 4th edition, 2004, ISBN: 0-7216-9688-0.
[9] *National Institute for Biological Standards and Control*; Potters Bar, UK. www.nibsc.ac.uk
[10] Sesardic et al. (2001) *Biologicals* 29:107-22.
[11] NIBSC code: 98/560.
[12] Module 1 of WHO's *The immunological basis for immunization series* (Galazka).
[13] NIBSC code: 69/017.
[14] NIBSC code: DIFT.
[15] *National Institute for Biological Standards and Control*; Potters Bar, UK. www.nibsc.ac.uk
[16] Sesardic et al. (2002) *Biologicals* 30:49-68.
[17] NIBSC code: 98/552.
[18] Module 1 of WHO's *The immunological basis for immunization series* (Galazka).
[19] NIBSC code: TEFT.
[20] Rappuoli et al. (1991) *TIBTECH* 9:232-238.
[21] Paoletti et al. (2001) *Vaccine* 19:2118-2126.
[22] WO00/56365.
[23] Gennaro (2000) *Remington: The Science and Practice of Pharmacy*. 20th edition, ISBN: 0683306472.
[24] WO01/41800.
[25] WO03/009869.
[26] Almeida & Alpar (1996) *J. Drug Targeting* 3:455-467.
[27] Agarwal & Mishra (1999) *Indian J Exp Biol* 37:6-16.
[28] WO00/53221.
[29] Jakobsen et al. (2002)*Infect Immun* 70:1443-1452.
[30] Bergquist et al. (1998) *APMIS* 106:800-806.
[31] Baudner et al. (2002) *Infect Immun* 70:4785-4790.
[32] Ugozzoli et al. (2002) *J Infect Dis* 186:1358-1361.
[33] Nony et al. (2001) *Vaccine* 27:3645-51.
[34] U.S. Pat. No. 6,355,271.
[35] WO00/23105.
[36] *Vaccine Design* . . . (1995) eds. Powell & Newman. ISBN: 030644867X. Plenum.
[37] Glezen & Alpers (1999) *Clin. Infect. Dis.* 28:219-224
[38] Madoff et al. (1994) *J Clin Invest* 94:286-92.
[39] Paoletti et al. (1994) *Infect Immun* 62:3236-43.
40 Xing D, Markey K, Das R G, Feavers I. 2014. Whole-cell pertussis vaccine potency assays: the Kendrick test and alternative assays. Expert Rev Vaccines. 13(10):1175-82.
Geurtsen J, Dzieciatkowska M, Steeghs L, Hamstra H J, Boleij J, Broen K, Akkerman G, El Hassan H, Li J, Richards J C, Tommassen J, van der Ley P. 2009 Identification of a novel lipopolysaccharide core biosynthesis gene cluster in *Bordetella pertussis*, and influence of core structure and lipid A glucosamine substitution on endotoxic activity. Infect Immun. July; 77(7):2602-11
Pizza, M., Covacci, A., Bartoloni, A., Perugini, M., Nencioni, L., De Magistris, M. T., Villa, L., Nucci, D., Manetti, R., and Bugnoli M. (1989) Mutants of pertussis toxin suitable for vaccine development. Science 246, 497-500
Gianmarco Gasperini, Massimiliano Biagini, Vanessa Arato, Claudia Gianfaldoni, Alessandro Vadi, Nathalie Norais, Giuliano Bensi, Isabel Delany, Mariagrazia Pizza, Beatrice Arico', and Rosanna Leuzzi. 2018. Outer Membrane Vesicles (OMV)-based and Proteomics-driven Antigen Selection Identifies Novel Factors Contributing to *Bordetella pertussis* Adhesion to Epithelial Cells.
Misiak A., Wilk M. M., Raverdeau M., Mills K. H. 2017a. IL-17-Producing innate and pathogen-specific tissue resident memory γδ T cells expand in the lungs of *Bordetella pertussis*-infected mice. J Immunol, 198 pp. 363-374.
Misiak A, Leuzzi R, Allen A C, Galletti B, Baudner B C, D'Oro U, O'Hagan D T, Pizza M, Seubert A, Mills K H G. 2017b. Addition of a TLR7 agonist to an acellular pertussis vaccine enhances Th1 and Th17 responses and protective immunity in a mouse model. Vaccine. 2017 Sep. 18; 35(39):5256-5263.
Agnolon V, Bruno C, Leuzzi R., Galletti B., D'Oro U., Pizza M., Seubert A., O'Hagan D. T., Baudner B. C. 2015. The potential of adjuvants to improve immune responses against TdaP vaccines: a preclinical evaluation of MF59 and monophosphoryl lipid A. Int J Pharm, 492, pp. 169-176
Kendrick P L, Eldering G, Dixon M K, Misner J. Mouse protection tests in the study of pertussis vaccine: a comparative series using the intracerebral route for challenge. Am J Public Health Nations Health 1947; 37(7):803-10

The invention claimed is:

1. An immunogenic composition comprising (a) Outer Membrane Vesicles (OMVs), (b) an acellular pertussis antigen, (c) a tetanus toxoid and (d) a diphtheria toxoid, wherein the OMVs are derived from a *Bordetella pertussis* strain comprising an S1 gene which has been modified to include the mutations R9K and E129G and which expresses a genetically detoxified pertussis toxoid PT 9K/129G;

wherein the OMVs are not treated or chemically detoxified by treatment with formaldehyde, formalin, glutaraldehyde, hydrogen peroxide or a combination thereof.

2. The immunogenic composition according to claim 1, wherein the OMVs are derived from a *Bordetella pertussis* strain in which the ArnT gene has been knocked-out or deleted.

3. The immunogenic composition according to claim 1, wherein the Lipid A in the OMVs has a modified structure without glucosamine (GlcN) substitutions on the distal phosphate groups of the core structure.

4. The immunogenic composition according to claim 1, wherein the acellular pertussis antigen is selected from the group consisting of (i) detoxified pertussis toxin (PT), (ii) filamentous hemagglutinin (FHA) and (iii) pertactin (PRN).

5. The immunogenic composition according to claim 4, wherein the acellular pertussis antigen comprises PT, FHA and PRN.

6. The immunogenic composition according to claim 5, wherein the PT is a genetically detoxified pertussis toxoid.

7. The immunogenic composition according to claim 5, wherein PT, FHA and PRN are present at a ratio of 16:16:5 (measured by weight).

8. The immunogenic composition according to claim 1, wherein the diphtheria toxoid is present at a concentration of i. from 4 Lf/ml to 8 Lf/ml per 0.5 ml dose, or ii. from 20 to 50 Lf/ml per 0.5 ml dose.

9. The immunogenic composition according to claim 1, wherein tetanus toxoid is present at a concentration of from about 5 to about 10 Lf per 0.5 ml dose.

10. The immunogenic composition according to claim 1, wherein the diphtheria toxoid and tetanus toxoid are present:

i. at a diphtheria toxoid:tetanus toxoid ratio that is greater than 1, or ii. at a tetanus toxoid:diphtheria toxoid ratio that is greater than 1.

11. The immunogenic composition according to claim 1, wherein the immunogenic composition contains an adjuvant, optionally wherein the immunogenic composition contains an aluminium salt adjuvant.

12. The immunogenic composition according to claim 1, wherein the composition is for use as a medicament.

13. The immunogenic composition according to claim 1 for use in a method of raising an immune response in a patient, comprising the step of administering to the patient the composition.

14. The immunogenic composition according to claim 13 for use in a method of raising an immune response in a patient against *Corynebacterium diphtheriae, Clostridium tetani* and *Bordetella pertussis.*

15. A method of raising an immune response in a patient, comprising the step of administering to the patient the composition according to claim 1.

16. The method according to claim 15, wherein the immune response is against *Corynebacterium diphtheriae, Clostridium tetani* and *Bordetella pertussis.*

17. The immunogenic composition according to claim 8, wherein the diphtheria toxoid is present at a concentration of:

i. 4 Lf per 0.5 ml dose; or ii. 25 Lf per 0.5 ml dose.

18. The immunogenic composition according to claim 10, wherein the diphtheria toxoid and tetanus toxoid are present:

i. at a diphtheria toxoid:tetanus toxoid ratio that is between 2:1 and 3:1, or ii. at a tetanus toxoid:diphtheria toxoid ratio that is between 1.5:1 and 2.5:1.

19. The immunogenic composition according to claim 18, wherein the diphtheria toxoid and tetanus toxoid are present:

i. at a diphtheria toxoid:tetanus toxoid ratio that is 2.5:1, or ii. at a tetanus toxoid:diphtheria toxoid ratio that is 2:1.

* * * * *